(12) United States Patent
Prince

(10) Patent No.: US 7,710,611 B2
(45) Date of Patent: May 4, 2010

(54) SINGLE AND MULTI-SPECTRAL ILLUMINATION SYSTEM AND METHOD

(75) Inventor: David P. Prince, Wakefield, RI (US)

(73) Assignee: Illinois Tool Works, Inc., Glenview, IL (US)

( * ) Notice: Subject to any disclaimer, the term of this patent is extended or adjusted under 35 U.S.C. 154(b) by 608 days.

(21) Appl. No.: 11/707,757

(22) Filed: Feb. 16, 2007

(65) Prior Publication Data

US 2008/0197170 A1    Aug. 21, 2008

(51) Int. Cl.
*H04M 1/40* (2006.01)
(52) U.S. Cl. .................... 358/3.29; 382/144
(58) Field of Classification Search ................. 358/3.29, 358/1.9, 2.1, 1.15, 504, 406, 509, 475; 382/141, 382/144–152
See application file for complete search history.

(56) References Cited

U.S. PATENT DOCUMENTS

| | | |
|---|---|---|
| 5,058,178 A | 10/1991 | Ray |
| 5,060,063 A | 10/1991 | Freeman |
| 5,157,438 A | 10/1992 | Beale |
| 5,278,012 A | 1/1994 | Yamanaka et al. |
| RE34,615 E | 5/1994 | Freeman |
| 5,455,870 A | 10/1995 | Sepai et al. |
| 5,752,446 A | 5/1998 | Squibb |
| 5,943,089 A | 8/1999 | Douglas |
| 6,198,529 B1 | 3/2001 | Clark, Jr. et al. |
| 6,621,517 B1 | 9/2003 | Squibb |
| 6,738,505 B1 | 5/2004 | Prince |
| 6,810,138 B1 | 10/2004 | Schanz |
| 6,891,967 B2 | 5/2005 | Prince |
| 7,028,391 B2 | 4/2006 | Pham-Van-Diep et al. |
| 2007/0102477 A1 | 5/2007 | Prince |
| 2007/0175343 A1 | 8/2007 | Prince |

FOREIGN PATENT DOCUMENTS

GB    2 249 672 A    5/1992

(Continued)

OTHER PUBLICATIONS

Patent Abstracts of Japan JP 2006 242719 (Omron Corp.); Sep. 14, 2006; 1 pg.

(Continued)

*Primary Examiner*—Edward L Coles
*Assistant Examiner*—Stephen M Brinich
(74) *Attorney, Agent, or Firm*—Lando & Anastasi, LLP

(57) ABSTRACT

A stencil printer apparatus for depositing a solder paste onto the surface of the electronic substrate, comprising a frame, a stencil coupled to the frame, the stencil having a plurality of apertures, a dispenser coupled to the frame, the stencil and the dispenser being configured to deposit the solder paste onto the electronic substrate, an imaging system constructed and arranged to capture an image of the electronic substrate, and a controller coupled to the imaging system and configured to control movement of the imaging system to capture the image. The imaging system comprises a camera element configured to capture the image of at least the portion of the surface of the electronic substrate, and a first illumination element comprising a long-wavelength light source configured to illuminate at least the portion of the surface of the electronic substrate by generating long-wavelength light. Other embodiments and methods are disclosed.

57 Claims, 14 Drawing Sheets

FOREIGN PATENT DOCUMENTS

| | | |
|---|---|---|
| GB | 2 403 003 A | 12/2004 |
| WO | 2005083402 A1 | 9/2005 |

OTHER PUBLICATIONS

Patent Abstracts of Japan JP 2007 010497 (CKD Corp.); Jan. 18, 2007; 1 pg.

International Search Report for PCT/US2008/050068 mailed Aug. 21, 2008.

EKRA-EVA™ Vision-Systems; http://www.ekra.com/pages/eva.html; 1 pg., Jul. 25, 2005.

Patent Abstracts of Japan; JP 2002234131 A (Sony Corp.); Aug. 20, 2002, 1 pg.

International Search Report for PCT/US2006/043166 mailed Feb. 2, 2007, 3 pgs.

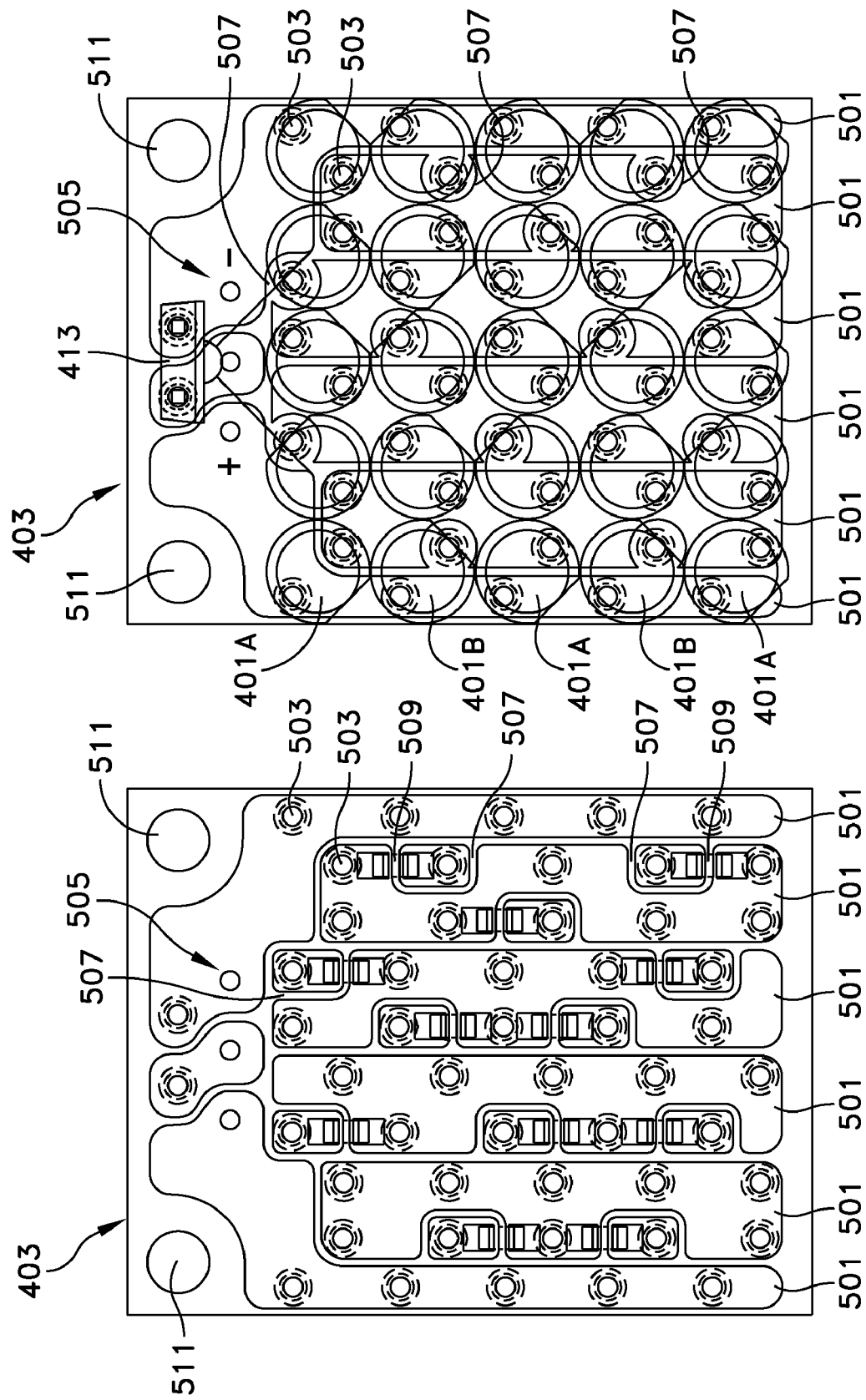

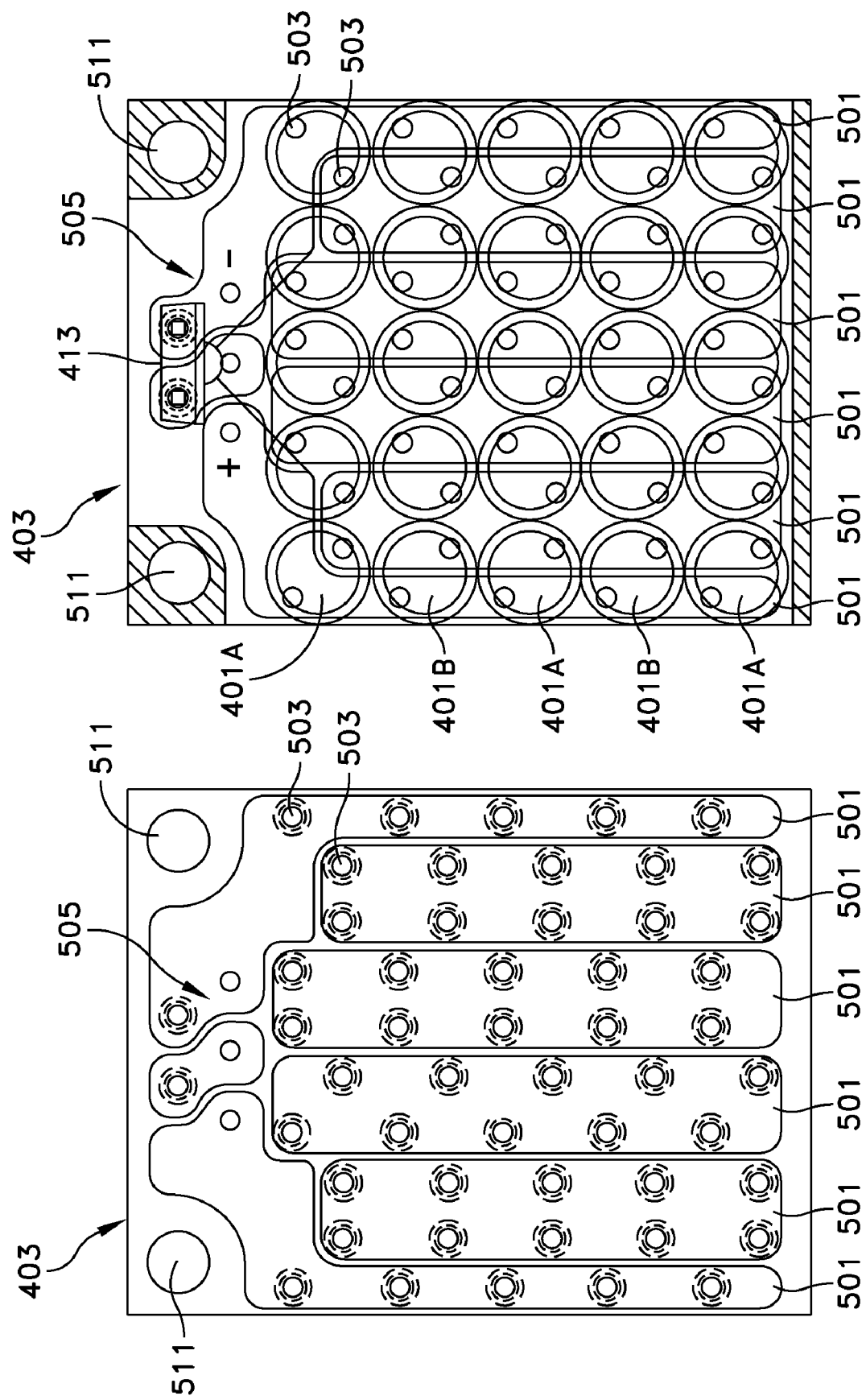

SINGLE AND MULTI-SPECTRAL ILLUMINATION SYSTEM AND METHOD

FIELD OF THE INVENTION

The invention relates to apparatuses and processes for dispensing material, and more particularly to an apparatus and process for printing solder paste through a screen or stencil printer onto an electronic substrate, such as a printed circuit board.

BACKGROUND

Circuit board manufacturing operations typically involve a stencil printer used to print solder paste onto a circuit board. Typically, a circuit board having a pattern of pads or other conductive surfaces onto which solder paste will be deposited is delivered into the stencil printer and one or more small holes or marks on the circuit board, called fiducials, is used to align the circuit board with a stencil or screen of the printer prior to the printing of solder paste onto the circuit board. After the circuit board is aligned, the board is raised to the stencil (or in some configurations, the stencil is lowered to the circuit board), solder paste is dispensed onto the stencil, and a wiper blade (or squeegee) traverses the stencil to force the solder paste through apertures formed in the stencil and onto the board.

In some prior art stencil printers, a dispensing head delivers solder paste between first and second wiper blades, wherein during a print stroke one of the wiper blades is used to move or roll solder paste across the stencil. The first and second wiper blades are used on alternating boards to continually pass the roll of solder paste over the apertures of a stencil to print each successive circuit board. The wiper blades are typically at an angle with respect to the stencil to apply downward pressure on the solder paste to force the solder paste through the apertures of the stencil. In other prior art stencil printers, the dispensing head is pressurized to force solder paste through the apertures, and the wiper blades are employed to scrape excess solder paste from the stencil during a print stroke.

After solder paste is deposited onto the circuit board, an imaging system is employed to take images of areas of the circuit board and/or the stencil for, in certain instances, the purpose of inspecting the accuracy of the deposit of solder paste on the pads of the circuit board. Another application of the imaging system involves the aforementioned aligning of the stencil and the circuit board prior to printing in order to register the openings of the stencil with the electronic pads of the circuit board. Such imaging systems are disclosed in U.S. Pat. Nos. RE34,615 and 5,060,063, both to Freeman, which are owned by the assignee of the invention and hereby incorporated herein by reference. Some improved imaging systems are disclosed in pending application Ser. No. 11/272,192, entitled IMAGING SYSTEM AND METHOD FOR A STENCIL PRINTER, filed on Nov. 10, 2005, to Prince, which is owned by the assignee of the invention and is hereby incorporated herein by reference.

Consistent modeling of solder paste on a substrate, e.g., the circuit board, is required to facilitate the optimum two-dimensional imaging performance of the vision system, as well as subsequent inspections based on these images, irrespective of variations in geometry, definition, or general qualities of the deposit being imaged. Well-defined solder paste deposits have nearly vertical sides and relatively flat top surfaces that are perpendicular to the optical viewing axis (i.e., an axis generally perpendicular to a plane of the circuit board). Finely textured paste surfaces having this generally perpendicular orientation may be imaged with relative consistency using traditional illumination techniques that illuminate surfaces with on-axis white light. With on-axis illumination, the strongest components of scattered light from the top surface of the solder paste deposit are directed back along the optical viewing path and are collected by the imaging system.

In contrast, when on-axis illumination strikes a surface that is not generally perpendicular to the angle of incidence, the strongest components of scattered light from the surface are directed away, or off-axis, from the optical or on-axis viewing path and are not collected by the imaging system. Specifically, the sloped sides and irregular top surfaces of poorly shaped solder paste deposits are less efficiently illuminated and therefore more difficult to view using only on-axis illumination only.

With white light, a range of wavelengths of visible light is reflected either on-axis or off-axis from the surface (i.e., depending on the shape of the surface). Such white light is generally strongly reflected on-axis by pads having no solder paste deposits because such pads typically are clean and perpendicular to the viewing path. However, recent use of sacrificial and protective coatings to keep the pads of a substrate clean has decreased the level of on-axis reflection from pads having no solder paste deposits. This decrease in reflection makes differentiation between pads without solder paste deposits and with solder paste deposits more difficult.

SUMMARY

The invention will be more fully understood after a review of the following figures, detailed description and claims.

One aspect of the invention includes a stencil printer apparatus for depositing a solder paste onto the surface of the electronic substrate. In some embodiments, the stencil printer comprises a frame; a stencil coupled to the frame, the stencil having a plurality of apertures; a dispenser coupled to the frame, the stencil and the dispenser being configured to deposit the solder paste onto the electronic substrate; an imaging system constructed and arranged to capture an image of the electronic substrate, the imaging system comprising a camera element configured to capture the image of at least the portion of the surface of the electronic substrate, and a first illumination element comprising a long-wavelength light source configured to illuminate at least the portion of the surface of the electronic substrate by generating long-wavelength light; and a controller coupled to the imaging system and configured to control movement of the imaging system to capture the image.

In some embodiments, the long-wavelength light includes infrared light. In some embodiments, the infrared light includes near-infrared light. In some embodiments, the long-wavelength light includes light having a wavelength greater than about 670 nanometers. In some embodiments, the long-wavelength light includes light having a wavelength less than about 825 nanometers. In some embodiments, the long-wavelength light includes light having a wavelength of about 735 nanometers.

In some embodiments, the long-wavelength light source comprises at least one long-wavelength LED configured to generate the long-wavelength light. In some implementations, the at least one long-wavelength LED includes a plurality of long-wavelength LEDs. In some embodiments, the first illumination element further comprises a white light source configured to illuminate at least the portion of the surface of the electronic substrate by generating white light. In some embodiments, the long-wavelength light source comprises at least one long-wavelength LED configured to generate the long-wavelength light and the white light source comprises at least one white LED configured to generate the white light.

In some embodiments, the first illumination element is configured such that when generating the long-wavelength light and the white light, at least one first circuit branch to which the at least one long-wavelength LED is coupled and at least one second circuit branch to which the at least one white LED is coupled both experience a substantially similar current. In some implementations, the substantially similar current is about eighty milliamps. In some implementations, the first illumination element includes at least one resistor coupled to at least one of the at least one first circuit branch and the at least one second circuit branch such that when generating the long-wavelength light and the white light, the at least one first circuit branch and the at least one second circuit branch experience the substantially similar current In some embodiments, the first illumination element is configured to illuminate at least the portion of the surface of the electronic substrate by substantially simultaneously generating the white light and the long-wavelength light. In some embodiments, the first illumination element includes an on-axis illumination element configured to generate the long-wavelength light substantially along a first axis that is generally perpendicular to the surface of the electronic substrate. Some embodiments further comprise an off-axis illumination element configured to generate light substantially along a second axis that extends at an angle with respect to the first axis. In some implementations, the on-axis illumination element further comprises a white light source configured to illuminate at least the portion of the surface of the electronic substrate by generating white light substantially along the first axis.

In some embodiments, the first illumination element further comprises at least one diffuser configured such that the long-wavelength light substantially uniformly illuminates at least the portion of the electronic substrate. In some embodiments, the image includes a representation of solder paste on a pad of the electronic substrate. In some embodiments, the controller includes a processor configured to perform a first contrast recognition process on the image to determine the accuracy of a desired solder paste deposit on at least one pad of the electronic substrate. In some implementations, the imaging system is further configured to capture an image of the stencil, and the processor is further configured to perform a second contrast recognition process on the image of the stencil to detect an undesired solder paste deposit on the stencil.

Another aspect of the invention includes an imaging apparatus for capturing an image of at least a portion of a surface of an electronic substrate. In some embodiments, the imaging apparatus comprises a camera element configured to capture the image of at least the portion of the surface of the electronic substrate, and a first illumination element comprising a long-wavelength light source configured to illuminate at least the portion of the surface of the electronic substrate by generating long-wavelength light.

In some embodiments, the long-wavelength light includes infrared light. In some embodiments, the infrared light includes near-infrared light. In some embodiments, the long-wavelength light includes light having a wavelength greater than about 670 nanometers. In some embodiments, the long-wavelength light includes light having a wavelength less than about 825 nanometers. In some embodiments, the long-wavelength light includes light having a wavelength of about 735 nanometers.

In some embodiments, the long-wavelength light source comprises at least one long-wavelength LED configured to generate the long-wavelength light. In some implementations, the at least one long-wavelength LED includes a plurality of long-wavelength LEDs. In some embodiments, the first illumination element further comprises a white light source configured to illuminate at least the portion of the surface of the electronic substrate by generating white light. In some embodiments, the long-wavelength light source comprises at least one long-wavelength LED configured to generate the long-wavelength light and the white light source comprises at least one white LED configured to generate the white light.

In some embodiments, the first illumination element is configured such that when generating the long-wavelength light and the white light, at least one first circuit branch to which the at least one long-wavelength LED is coupled and at least one second circuit branch to which the at least one white LED is coupled both experience a substantially similar current. In some implementations, the substantially similar current is about eighty milliamps. In some implementations, the first illumination element includes at least one resistor coupled to at least one of the at least one first circuit branch and the at least one second circuit branch such that when generating the long-wavelength light and the white light, the at least one first circuit branch and the at least one second circuit branch experience the substantially similar current. In some embodiments, the first illumination element is configured to illuminate at least the portion of the surface of the electronic substrate by substantially simultaneously generating the white light and the long-wavelength light.

In some embodiments, the first illumination element includes an on-axis illumination element configured to generate the long-wavelength light substantially along a first axis that is generally perpendicular to the surface of the electronic substrate. Some embodiments further comprise an off-axis illumination element configured to generate light substantially along a second axis that extends at an angle with respect to the first axis. In some implementations, the on-axis illumination element further comprises a white light source configured to illuminate at least the portion of the surface of the electronic substrate by generating white light substantially along the first axis.

In some embodiments, the first illumination element further comprises at least one diffuser configured such that the long-wavelength light substantially uniformly illuminates at least the portion of the electronic substrate. In some embodiments, the image includes a representation of solder paste on a pad of the electronic substrate. In some embodiments, the imaging system is further configured to capture an image of a stencil that includes a representation of undesired solder paste on the stencil.

Another aspect of the invention includes an imaging apparatus for capturing an image of at least a portion of a surface of an electronic substrate. In some embodiments, the imaging apparatus comprises a camera element configured to capture the image of at least the portion of the surface of the electronic substrate, and a first illumination element comprising means for illuminating at least the portion of the surface of the electronic substrate with long-wavelength light.

In some embodiments, the long-wavelength light includes infrared light. In some embodiments, the infrared light includes near-infrared light. In some embodiments, the long-wavelength light includes light having a wavelength greater than about 670 nanometers. In some embodiments, the long-wavelength light includes light having a wavelength less than about 825 nanometers. In some embodiments, the long-wavelength light includes light having a wavelength of about 735 nanometers.

In some embodiments, the first illumination element further comprises a white light source configured to illuminate at least the portion of the surface of the electronic substrate with white light. In some embodiments, the means for illuminating the at least the portion of the surface includes an on-axis means for illuminating the at least the portion of the surface by generating the long-wavelength light substantially along a first axis that is generally perpendicular to the surface of the electronic substrate. Some embodiments further comprise an off-axis illumination element configured to generate light substantially along a second axis that extends at an angle with respect to the first axis. In some implementations, the on-axis means further comprises a white light source configured to illuminate at least the portion of the surface of the electronic substrate with white light.

In some embodiments, the means for illuminating at least the portion of the surface of the electronic substrate comprises at least one long-wavelength LED. In some embodiments, the means for illuminating at least the portion of the surface of the electronic substrate further comprises a diffuser configured so that the long-wavelength light substantially uniformly illuminates the portion of the electronic substrate.

Yet another aspect of the invention includes a method of dispensing a solder paste onto a surface of an electronic substrate. In some embodiments, the method comprises delivering the electronic substrate to a stencil printer, depositing the solder paste onto the surface of the electronic substrate, illuminating at least a portion of the surface of the electronic substrate with long-wavelength light that is generated by a long-wavelength light source, and capturing an image of at least the portion of the surface of the electronic substrate.

In some embodiments, the long-wavelength light includes infrared light. In some embodiments, the infrared light includes near-infrared light. In some embodiments, the long-wavelength light includes light having a wavelength greater than about 670 nanometers. In some embodiments, the long-wavelength light includes light having a wavelength less than about 825 nanometers. In some embodiments, the long-wavelength light includes light having a wavelength of about 735 nanometers.

Some embodiments further comprise determining an accuracy of a solder paste deposit on the surface of the electronic substrate. In some embodiments, determining the accuracy of the solder paste deposit includes comparing at least a portion of the image to at least one threshold value. Some embodiments further comprise illuminating at least the portion of the surface of the electronic substrate with white light.

Some embodiments further comprise directing the long wavelength light substantially along a first axis that is generally perpendicular to the surface of the electronic substrate. Some embodiments further comprise illuminating at least the portion of the surface of the electronic substrate with light directed substantially along a second axis that extends at an angle with respect to the first axis. Some implementations further comprise illuminating at least the portion of the surface of the electronic substrate with white light directed substantially along the first axis.

BRIEF DESCRIPTION OF THE DRAWINGS

In the drawings, like reference characters refer to the same or similar parts throughout the different views. The drawings are not necessarily to scale, emphasis instead being placed upon illustrating particular principles, discussed below.

FIGS. 5A and 5B are views of a printed circuit board that may be used in the illumination device of FIG. 4 in accordance with some embodiments of the invention;

FIGS. 6A and 6B are views of an alternative printed circuit board that may be used in the illumination device of FIG. 4 in accordance with some embodiments of the invention;

DETAILED DESCRIPTION

Figure 1:
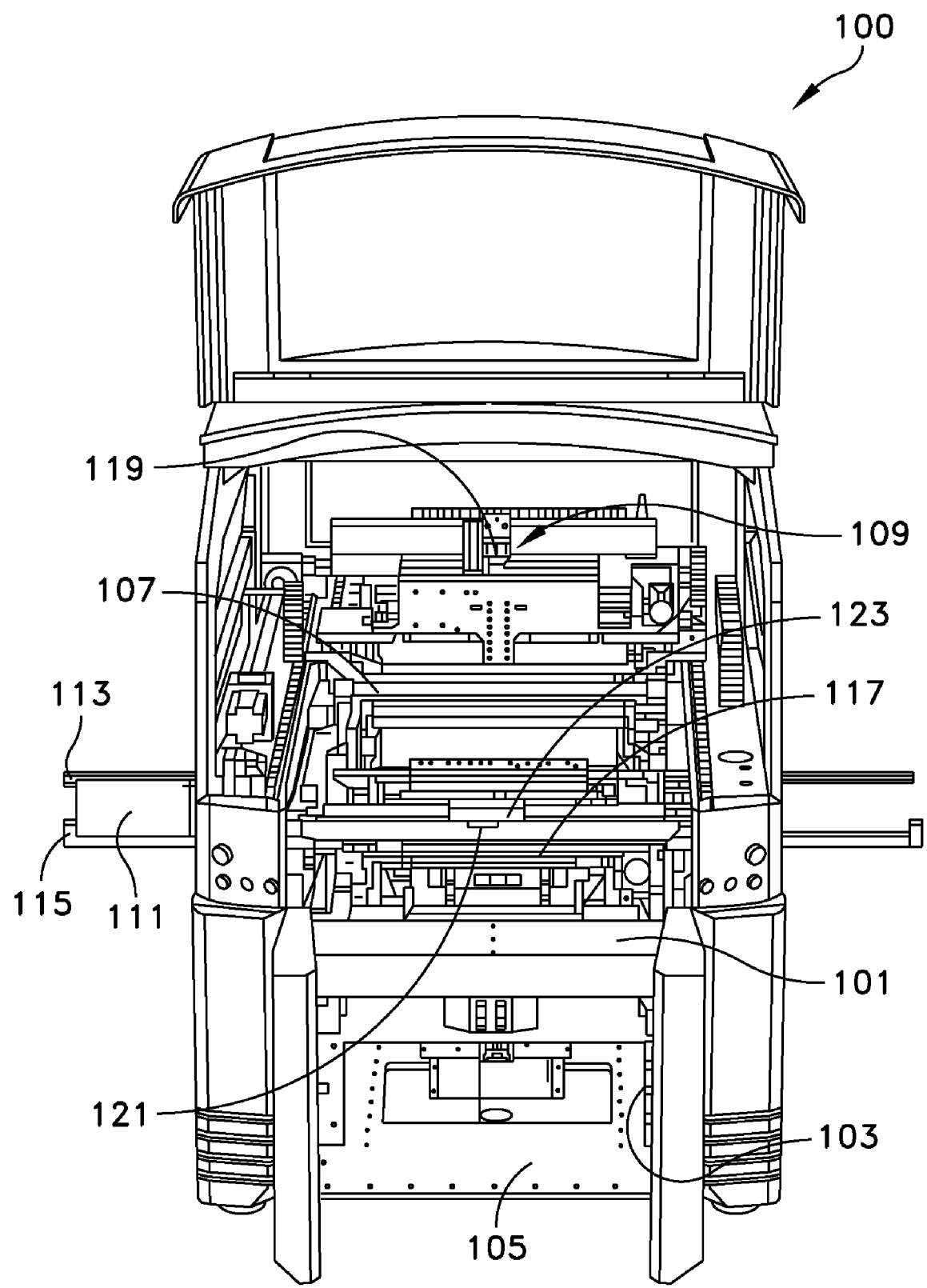
FIG. 1 is a perspective view of a stencil printer in accordance with some embodiments of the invention.

Embodiments of the invention are not limited in application to the details of construction and the arrangement of components and acts set forth in the following description or illustrated in the drawings. The invention may be capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

For purposes of illustration, embodiments of the invention will now be described with reference to a stencil printer used to print solder paste onto a circuit board. One skilled in the art will appreciate that embodiments of the invention are not limited to stencil printers that print solder paste onto circuit boards, but rather, may be used in other applications requiring dispensing of other viscous materials, such as glues, encapsulents, underfills, and other assembly materials suitable for attaching electronic components onto a circuit board. Thus, any reference to solder paste herein contemplates use of such other materials. Also, the terms "screen" and "stencil" may be used interchangeably herein to describe a device in a printer that defines a pattern to be printed onto a substrate.

FIG. 1 shows a front perspective view of a stencil printer, generally indicated at 100, in accordance with one embodiment of the invention. The stencil printer 100 may include a frame 101 that supports components of the stencil printer 100 including a controller 103 located in a cabinet 105 of the stencil printer 100, a stencil 107, and a dispensing head, generally indicated at 109, for dispensing solder paste. The dispensing head 109 may be movable along orthogonal axes by a gantry system (not designated) under the control of the controller 103 to allow printing of solder paste on a circuit board 111.

In some embodiments, the stencil printer 100 may also include a conveyor system having rails 113, 115 for transporting the circuit board 111 to a printing position in the stencil printer 100. In some implementations, the stencil printer 100 has a support assembly 117 (e.g., pins, gel membranes, etc.) positioned beneath the circuit board 111 when the circuit board 111 is in the dispensing position. The support assembly 117 may be used to raise the circuit board 111 off of the rails 113, 115 to place the circuit board 111 in contact with, or in close proximity to, the stencil 107 when printing (i.e., solder paste depositing) is to occur.

In one embodiment, the dispensing head 109 may be configured to receive at least one solder paste cartridge 119 that provides solder paste to the dispensing head during a printing operation. In one embodiment, the solder paste cartridge 119 is coupled to one end of a pneumatic air hose in a well-known manner. The other end of the pneumatic air hose may be attached to a compressor contained within the frame 101 of the stencil printer 100 that, under the control of the controller 103, provides pressurized air to the cartridge 119 to force solder paste into the dispensing head 109 and onto the stencil 107. Other configurations for dispensing solder paste onto the stencil 107 may also be employed. For example, in other embodiments, mechanical devices, such as a piston, may be used in addition to, or in place of, air pressure to force the solder paste from the cartridge 119 into the dispensing head 109. In yet another embodiment, the controller 103 may be implemented using a personal computer having a suitable operating system (e.g., Microsoft® DOS, Windows® NT, Windows Vista, UNIX, etc.) with application specific software to control the operation of the stencil printer 100 as described herein.

In some embodiments, the stencil printer 100 may operate as follows. The circuit board 111 may be loaded into the stencil printer 100 in a print position using the conveyor rails 113, 115 and by aligning the circuit board with the stencil. The dispensing head 109 may then be lowered in the Z-direction until it is in contact with the stencil 107. The dispensing head 109 may fully traverse the stencil 107 in a first print stroke to force solder paste through apertures of the stencil 107 and onto the circuit board 111. Once the dispensing head 109 has fully traversed the stencil 107, the circuit board 111 may be transported by the conveyor rails 113, 115 from the stencil printer 100 so that a second, subsequent circuit board may be loaded into the stencil printer 100. To print on the second circuit board, the dispensing head 109 may be moved in a second print stroke across the stencil 107 in an opposite direction to that used for the first circuit board 111.

Figure 2:
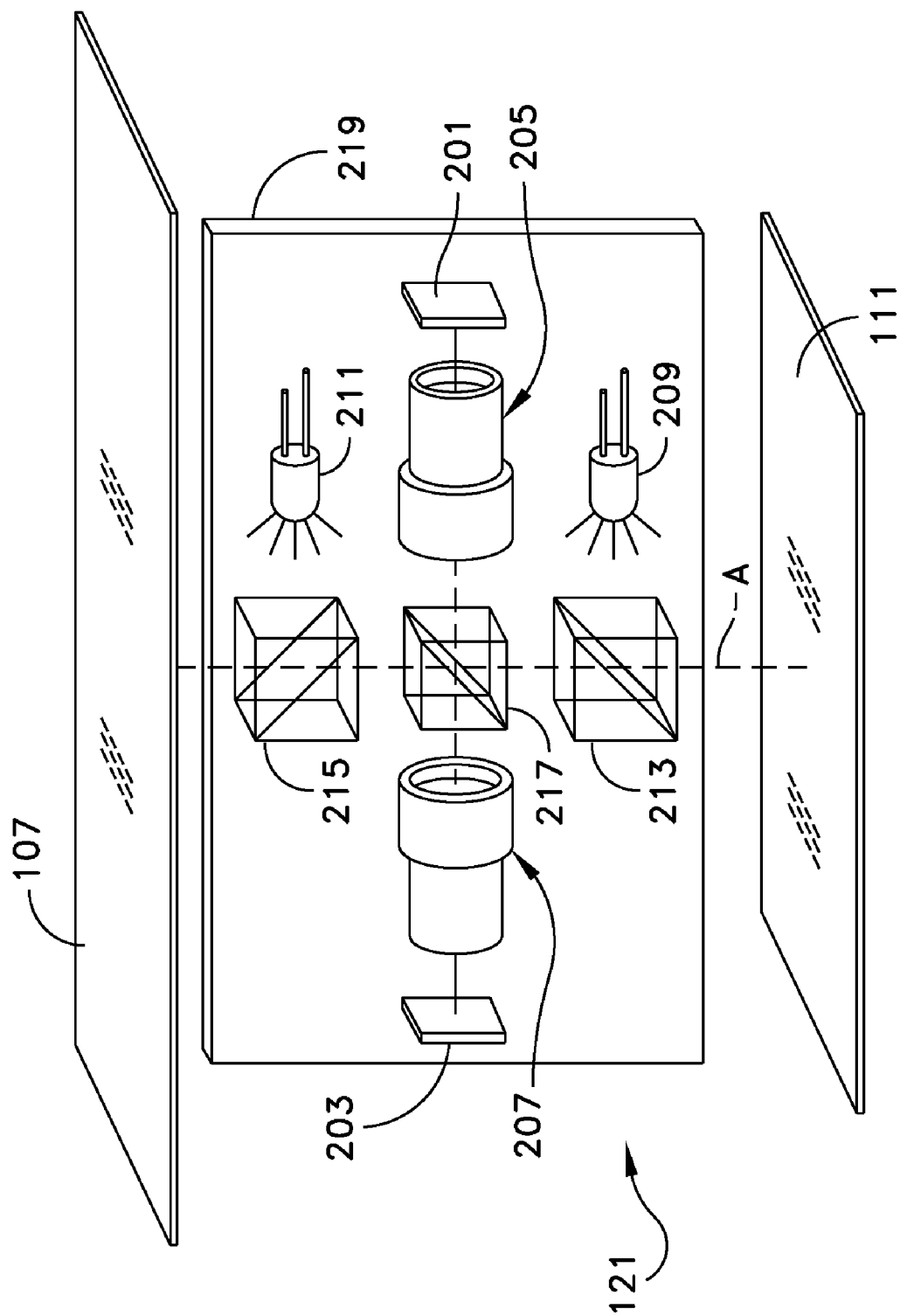
FIG. 2 is a diagram of an imaging system in accordance with some embodiments of the invention.

Referring to FIG. 2 in addition to FIG. 1, an exemplary imaging system of an embodiment of the invention is generally designated at 121. As shown, in this exemplary embodiment, the imaging system 121 is disposed between the stencil 107 and the circuit board 111, which in turn is supported by the support assembly 117 (FIG. 1). The imaging system 121 may be coupled to a gantry system 123 (FIG. 1), which may be part of the gantry used to move the dispensing head 109 or provided separately within the stencil printer 100. The construction of the gantry system 123 used to move the imaging system 121 is well-known in the art of inspection within a solder printer (e.g., 100). The arrangement may be such that the imaging system 121 may be located at any position below the stencil 107 and above the circuit board 111 to capture an image of predefined areas of the circuit board 111 or the stencil 107, respectively. In other embodiments, when positioning the imaging system 121 outside the printing nest, the imaging system 121 may be located above or below the stencil 107 and/or the circuit board 111.

As shown in FIG. 2, in one exemplary embodiment, the imaging system 121 comprises an optical assembly having two cameras 201, 203, two lens assemblies generally indicated at 205, 207, two illumination devices 209, 211, two beam splitters 213, 215, and a mirror assembly 217. In certain embodiments, the camera and a lens assembly may be configured together as a camera assembly. Such an assembly as well as the imaging system 121 may also be referred to as a camera probe. A frame 219 may support the components of the imaging system 121. In some embodiments, the cameras 201, 203 may be identical in construction with respect to one another, and, in one embodiment, each camera may be a digital CCD camera of the type that may be purchased from Opteon Corporation of Cambridge, Mass. Each camera may be either a color camera or a black and white camera. In one implementation in which black and white cameras are used, a 652 by 494 pixel WaferCam model B1A from Opteon Corporation may be used. In one implementation, if higher resolution is desired, a 1024 by 768 pixel WaferCam model B1J from Opteon Corporation may be used. In one implementation in which color cameras are used, a 1024 by 768 pixel WaferCam Model C1J from Opteon Corporation may be used. In other embodiments, CMOS cameras may be used. In one such embodiment, the uEye model 1226-LE-M available from IDS Imaging Development Systems GHMH of Obersulm, Germany.

In one embodiment, the illumination devices 209, 211 may include one or more light emitting diodes (LEDs) that are capable of generating an intense amount of light at their respective beam splitter 213 or 215, and are described in more detail below. The beam splitters 213, 215 and the mirror assembly 217, which may be a dual mirror with zero beam split, are well known in the art. In other embodiments, xenon and halogen lamps may be used to generate the light required. In other embodiments, fiber optics may be used to convey light from a remote source to the point of use.

The beam splitters 213, 215 may be designed to reflect a portion of the light generated by their respective illumination devices 209, 211 along a generally vertical axis A toward the circuit board 111 and the stencil 107, respectively, while further allowing a portion of the light reflected by the circuit board and the stencil to pass through to the mirror assembly 217. As used herein, the illumination device 209, and the beam splitter 213 (as well as the illumination device 211 and the beam splitter 215) may be referred to as an on-axis illumination assembly, which is configured to direct light substantially along or parallel to the axis A, which is generally perpendicular to a plane of the circuit board 111. In some embodiments, reflected light from the circuit board 111 travels back through the beam splitter 213 and on to the mirror assembly 217 where it is redirected toward the lens assembly 205 in order to capture an image of a predefined area of the circuit board.

The optical paths defined between the illumination devices 209, 211 and their respective cameras 201, 203 by means of beam splitters 213, 215 and mirror assembly 217 are well known to a person skilled in the art. As shown, the light reflected by the beam splitters 213, 215 toward their respective objects (i.e., the circuit board 111 and the stencil 107, respectively) extends substantially along or parallel to the axis A that is generally normal to the plane of the object.

Figure 3:
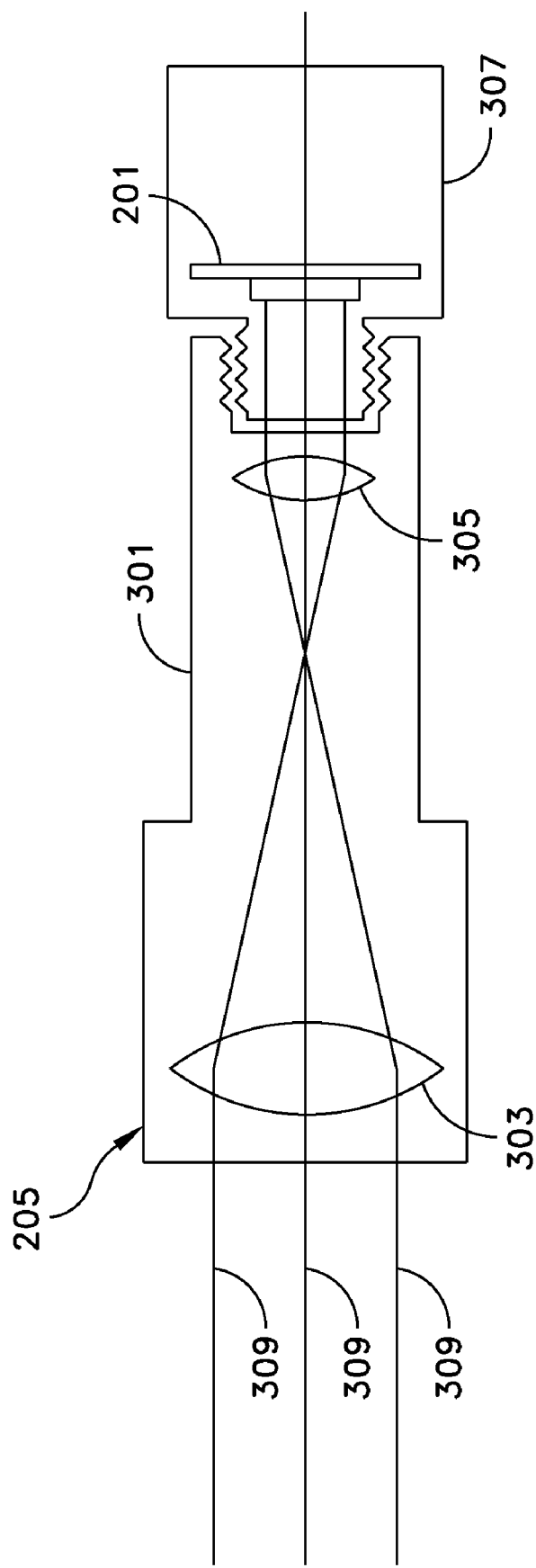
FIG. 3 is a diagram of a camera and lens assembly in accordance with some embodiments of the invention.

Referring to FIG. 3, the example camera 201 and the example lens assembly 205 are illustrated. As discussed above, the camera 203 may be identical or substantially similar in construction to the camera 201. In addition, the construction of the lens assembly 207 may be identical or substantially similar in construction to the lens assembly 205. Accordingly, the following discussion of the camera 201 and the lens assembly 205 generally applies for the camera 203 and the lens assembly 207, respectively, and, as discussed above, such an assembly may be referred to as a camera assembly or video probe.

As shown schematically in FIG. 3, the lens assembly 205 may include a housing 301, a pair of lenses 303, 305 disposed within the housing and an aperture (not shown) disposed between the lenses. The lenses 303, 305 together may provide a telecentric capability of the lens assembly 205. The collective lens assembly 205 may also be referred to as a "lens" or a "telecentric lens assembly."

In some embodiments, the arrangement is such that light reflected from the mirror assembly 217 of FIG. 2 is directed to the lens assembly 205. Once in the lens assembly 205, the light passes through the first lens 303, through the aperture (not shown), through the second lens 305, and on to the light-sensitive region of the camera 201, where the image is formed. In one embodiment the CCD reader of the camera 201 may include an electronic shutter. The camera 201, in part due to the telecentric lens assembly, may be designed to view an entire predefined area without exhibiting significant distortion in any part of the image.

As shown in FIG. 3, the camera 201 may be supported by a housing 307, which may be threadably attached to the housing 301 of the lens assembly 205. The housing 301 of the lens assembly 205 and the housing 307 of the camera 201 may be in axial alignment with one another so that the image, which is represented in ray-form by lines 309, is accurately directed toward the camera. The housing 301 of the lens assembly 205 may be suitably secured to the frame 219 of the imaging system 121.

In some embodiments, the arrangement may be such that when taking an image of the circuit board 111, the illumination device 209 generates an intense amount of light toward its respective beam splitter 213. This light may then be reflected by the beam splitter 213 toward the circuit board 111, and then reflected back toward the mirror assembly 217. The mirror assembly 217 may then direct the light through the lens assembly 205 and to the camera 201, which may capture the image of the predefined area of the circuit board 111. The image may be electronically stored (e.g., in RAM or other memory of controller 103) or used in real-time so that the image may be manipulated and analyzed by the controller 103 to detect a defective solder paste deposit or compared to an area of the stencil 107 for alignment purposes, or inspect a substrate for identification or tracking purposes, for example.

Similarly, in some embodiments, when taking an image of the stencil 107, the illumination device 211 may generate a beam of light that is directed toward its respective beam splitter 215. The light may then be directed toward the stencil 107 and reflected back through the beam splitter 215 to the mirror assembly 217. The light may then be directed toward the telecentric lens assembly 207 and on to the camera 203 to capture the image of the predefined area of the stencil 107. Once captured, the area of the stencil 107 may be analyzed by the controller 103 for inspection purposes to detect an undesired solder paste deposit (e.g., detecting clogged apertures in the stencil or surface contamination such as solder paste or resin, for example), or compared to an area of the circuit board 111 for alignment purposes.

The inspection capability of the imaging system 121 will be described in greater detail below.

As discussed above with respect to capturing an image of an area of the circuit board, the illumination device 209 shown in FIG. 2 may be configured to direct light along or parallel to the axis A normal to the plane of the circuit board. Thus, the camera 203 may be adapted to only capture images of light reflected from surfaces on the circuit board 111 that are normal to the direction of the light emitted onto the circuit board. Irregular, rounded or faceted surfaces, i.e., surfaces of solder paste deposits that are at an angle with respect to the plane of the circuit board, have a tendency to become less prominent as light is reflected away from the optical path.

In some embodiments, threshold-based imaging techniques (e.g., techniques that may be used by the processor controlling the imaging system 121 to analyze a captured image) may take advantage of this change in prominence to determine if solder paste has been deposited on a surface (e.g., a pad). For example, in some embodiments, a pad or portion of a pad without a solder paste deposit may appear bright in a captured image of a circuit board because light is predominantly reflected from the pad along the axis A. In contrast, a pad or portion of a pad with a solder paste deposit may appear dark in the captured image of the circuit board because light scattered by the angled surfaces of the solder paste deposit is not reflected to as great a degree along the axis A. In some embodiments, a brightness level at an image location corresponding to a pad or portion of a pad may be compared to a threshold value to determine if a solder paste deposit is present. Such thresholding techniques are well-known in the art.

Thresholding techniques have generally worked well to differentiate pads or portions of pads with solder paste deposits from pads or portions of pads without solder paste deposits when the pads of a circuit board are provided to the stencil printer 100 in a clean/reflective state. Because reflective pads without solder paste deposits cause more light to reflect along the axis A thereby causing the pads to appear brighter in images of the circuit board 111, such reflective pads may be relatively easily differentiated.

Increasingly, however, many substrates (e.g., circuit board 111) are being manufactured or pre-processed so that pads are coated with a non-reflective or less-reflective (i.e., less reflective than uncoated pads) coating. Common coatings may include an organic solderability preservative (OSP) or a resin. Such coatings may absorb or scatter light thereby decreasing the amount of light reflected along the axis A and then back towards the camera. This reduction in reflected light makes such coated pads appear darkened in images even when no solder paste deposits are present. Because of this darkened appearance, differences in brightness levels between pads or portions of pads with solder paste deposits and pads or portions of pads without solder paste deposits may be small or non-existent. Traditional thresholding techniques may therefore be less effective or ineffective in differentiating pads or portions of pads with solder paste deposits from pads or portions of pads without solder paste deposits.

In one aspect of the invention, it is recognized that long-wavelength light may be used to improve traditional thresholding techniques for use with pads coated with such non-reflective or less-reflective coatings. In particular, it is recognized that long-wavelength light may penetrate thin layers of these coatings such as those that are typically present on modern circuit boards (e.g., 111). Such long-wavelength light may then be reflected as usual by the underlying pad, and be reflected back along axis A. The long-wavelength light may penetrate the coating a second time as the long-wavelength light travels from the pad back along axis A. In contrast, traditionally used white light generally will not penetrate such coatings or will penetrate such coating to a lesser degree causing greater absorption and scattering of white light by the coatings and less reflection along axis A.

In some embodiments, any long-wavelength light may be used. In some embodiments, long-wavelength light may include infrared light. In some embodiments, the infrared light may include near-infrared light. In some embodiments, the long-wavelength light may include light having a wavelength greater than approximately six hundred seventy nanometers. In some implementations, the long-wavelength light may include light having a wavelength greater than approximately seven hundred nanometers. In some implementations, the long-wavelength light may include light having a wavelength less than three micrometers. In some implementations, the long-wavelength light may include light having a wavelength less than approximately eight hundred twenty-five nanometers. In one implementation, the long-wavelength light may include light having a wavelength of approximately seven hundred thirty-five nanometers.

Figure 4:
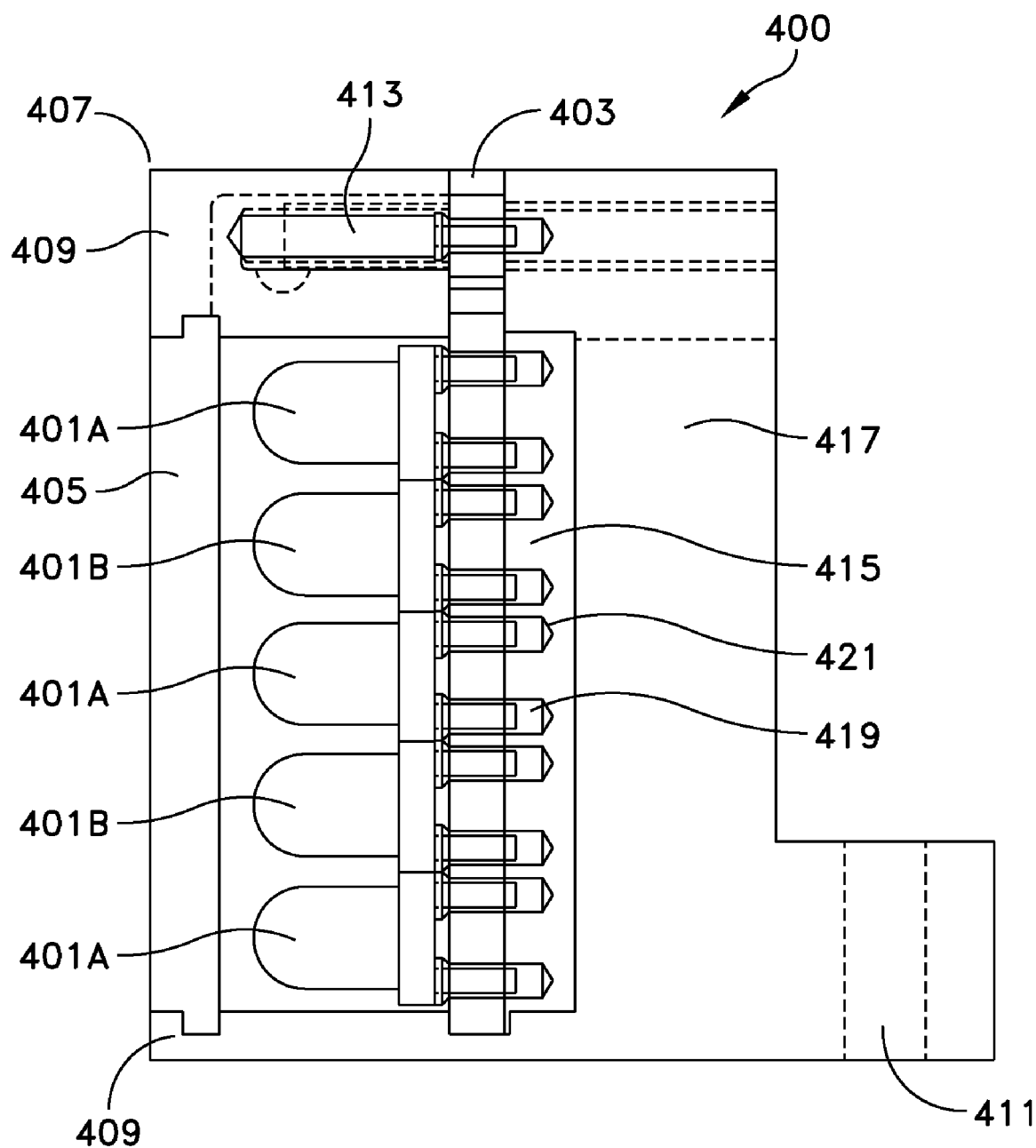
FIG. 4 is a diagram of an illumination device in accordance with some embodiments of the invention.

FIG. 4 illustrates one example illumination device 400 that may be used to generate the long-wavelength light and may be used as one or both of the illumination devices 209 and 211 of FIG. 2. Because stencil inspection may sometimes not benefit from long-wavelength illumination, in some implementations, illumination device 209, which illuminates the circuit board, may include long-wavelength light sources, as described below, but illumination device 211, which illuminates the stencil, may not include such long-wavelength light sources. In other implementations, both of the illumination devices 209, 211 may include long-wavelength light sources.

The example illumination device 400 includes a plurality of light sources, indicated at 401A and 401B. Some or all of the light sources 401A, 401B may generate long-wavelength light for illuminating the circuit board 111. The light sources 401A, 401B may be coupled to a printed circuit board substrate 403 that may be configured to connect to a power supply (not shown) and energize the light sources 401A, 401B. A diffuser 405 may be configured to diffuse light generated by the light sources so that a circuit board being illuminated by the light sources may be substantially uniformly illuminated. The light sources 401A, 401B may be housed in a housing 407. The housing 407 may include a diffuser lip 409 that holds the diffuser 405 in place and that may allow the diffuser to be removed to provide access to the light sources 401A, 401B. The housing 407 may also include an attachment bolt 411 that may be used to attach the illumination device 400 to the imaging system 121 (e.g., to the frame 219).

In some embodiments, each of the light sources 401A, 401B may be a long-wavelength light source. In such an embodiment, the light sources 401A, 401B may include a plurality of long-wavelength LED. The long-wavelength LEDs may be configured to generate long-wavelength light that may be directed along the axis A (e.g., by a beam splitter, as described above). In some implementations, each of the long-wavelength LEDs may generate an illumination having radiant intensity between approximately fifteen and approximately one hundred twenty milliwatts per steradian when operated continuously. In one particular implementation, the long-wavelength LEDs may include one or more L735-AU IR LEDs commercially available from Marubeni Corporation of Tokyo, Japan.

In other embodiments, a first set of the light sources 401A may be long-wavelength light sources and a second set of the light sources 401B may be white light sources (or some other desired visible light sources, such as red, green, blue light sources). Such a combination of long-wavelength light and white light may be useful because long-wavelength light alone may cause images to appear dull (i.e., missing fine details and sharp edges). A combination of long-wavelength light and white light may be used to capture a sharp image that may be used to differentiate pads coated with non-reflective or less-reflective coatings that have solder paste deposits from such pads without solder paste deposits using a single illumination device. This may be useful, for example, for detailed alignment of the stencil and the circuit board, bridge detection (i.e., detecting when solder paste deposits bridge a gap between two pads), or to read bar code or other identification marks from the stencil or circuit board (e.g., for identification/tracking of the stencil 107 or the circuit board 111), some of which may use texture-based and/or contrast-based solder paste detection techniques as described below. In some such embodiments, the first set of light sources 401A may be substantially similar to the light sources described above for embodiments in which all light sources are long-wavelength light sources. The second set of light sources 401B may include a plurality of white LEDs. In some implementations, the white LEDs may generate an illumination having a brightness of approximately two thousand millicandelas each in continuous operation. In one particular implementation, the plurality of white LEDs may include one or more NSPW310BS white LEDs available commercially from NICHIA of America Corporation of Detroit, Mich.

As mentioned above, in some embodiments, the illumination device 400 may include the diffuser 405. The diffuser 405 may be used to diffuse light generated by the light sources 401A, 401B so that light is approximately evenly output from the illumination device 400 thereby approximately evenly illuminating the circuit board. In some implementations, the diffuser may be made from translucent acrylic or glass. In one implementation, the diffuser may be made of an approximately two millimeter thick piece of Acrylite GP 051-6 acrylic available commercially from CYRO industries of Parsippany, N.J. In another implementation, the diffuser may be made of an approximately three millimeter thick piece of Acrylite FF 020-4 acrylic available commercially from CYRO industries.

In some embodiments, the illumination device 400 may include a photodiode 413. The photodiode may be used to monitor the output of the light sources 401A, 401B. In some embodiments, the monitored output may be used to adjust current applied to the light sources so that the light sources 401A, 401B generate a consistently bright output. In one particular implementation, the photodiode 413 may include a type OP950 PIN silicon photodiode available commercially from OPTEK, Inc. of Carrollton, Tex.

In particular with respect to LED light sources, the light sources 401A, 401B may generate a brighter light at the beginning of their useful lives than later in their useful lives. The photodiode 413 may be used to monitor the change in brightness throughout the useful lives of the light sources and transmit information to the controller 103 regarding the brightness of the light sources 401A, 401B. At the beginning of the useful lives of the light sources, the controller 103 may operate a power supply to decrease a level of current supplied to the light sources 401A, 401B, thereby decreasing the brightness of the light sources 401A, 401B. Towards the end of the useful lives of the light sources, the processor or controller may operate a power supply to increase a level of current supplied to the light sources, thereby increasing the brightness of the light sources 401A, 401B. In some implementations, the net effect may be an approximately even brightness level throughout the useful lives of the light source 401A, 401B.

Furthermore, brightness of some types of light sources 401A, 401B, such as LED light sources, may be affected in the short term by heat. For example, as an LED becomes hotter, the LED may also become dimmer. In some embodiments, the photodiode 413 may be configured to monitor short term brightness of the light sources 401A, 401B in addition to or as an alternative to long term brightness over the useful life of the light sources 401A, 401B as described above. For example, in some embodiments, the light sources 401A, 401B may be pulsed on for an amount of time that is long enough to capture an image of the circuit board 111. Over the course of that time, the light sources 401A, 401B may become hotter, and thereby also become dimmer. The photodiode may monitor the brightness of the light sources 401A, 401B during the time period and transmit a signal to the controller 103 indicating the brightness level. The controller 103 may control a power supply so that current may be reduced at the beginning of a pulse and increased throughout the pulse so that the brightness level of the light sources 401A, 401B remains approximately constant throughout the pulse.

To help control such heat generated by the light source, a heat conductive tape 415 may be coupled to the printed circuit board substrate 403 so that heat is dissipates away from the light sources 401A, 401B. The heat conductive tape 415 may include a heat conductive foam tape that may be used to provide thermal contact with a heat sink 417. In some implementations the heat conductive tape 415 may be about 0.1 inches thick. In some implementations, the heat conductive tape 415 may include Gap Pad VO Ultra Soft available commercially from The Bergquist Company of Chanhassen, Minn.

The heat sink 417 may also help dissipate heat from the light sources 401A, 401B to maximize the useful lives of the light sources 401A, 401B and decrease the variation in brightness of the light sources 401A, 401B during operation. In some implementations the heat sink 417 may include an aluminum bracket. In some implementations, the heat sink 417 may be used as a back portion of the housing 407. In some implementations, the attachment bolt 411 may be a part of the heat sink 417.

Referring now to FIGS. 4, 5A, 5B, 6A, and 6B, the light sources 401A, 401B may be coupled to the printed circuit board. Each light source may include two electrical leads (e.g., 419, 421) that may be inserted into two respective electrical sockets of the printed circuit board. In some implementations the two electrical leads may be about two millimeters long. Since some light sources may be sold by manufacturers with longer lead lengths, the leads may be cut to a desired length prior to assembly. FIG. 4 illustrates a view of these example connections. FIGS. 5A, SB, 6A, and 6B illustrate front and rear layers of the printed circuit board according to some embodiments of the invention.

FIG. 5A illustrates a front view of the light sources 401A, 401B arranged on the example printed circuit board substrate 403. As illustrated, the printed circuit board may include conductive (e.g., copper) traces 501 on the front side and a plurality of electrical sockets 503. The conductive traces may be electrically connected to the electrical leads of the LEDs through the electrical sockets 503 and a power supply (not shown) through a power input 505. The light sources 401A, 401B may be arranged so that positive leads one set of light sources are coupled to a first conductive trace and negative leads of that set of light sources are coupled to a second conductive trace. In some embodiments, as will be explained in more detail below, the conductive traces may include a non-conductive region 507 around some of the electric sockets so that the electrical leads of light sources coupled to those sockets are not directly coupled to the rest of the conductive traces 501.

FIG. 5B illustrates a rear view of the example printed circuit board substrate 403. As illustrated, the printed circuit board may include conductive traces 501 on the rear side. Such conductive traces 501 may be in addition to or as an alternative to the conductive traces 501 on the front side. In some implementations in which both front and rear conductive traces 501 are included, the electrical sockets 503 may be configured so that conductive traces on the front of the printed circuit board are electrically coupled to conductive traces on the back of the printed circuit board. In some implementations, including both front and rear conductive traces may improve heat dissipation away from the light sources 401A, 401B. Because high levels of heat may cause problems with some light sources 401A, 401B as described above, such improved heat dissipation may improve the useful life and reliability of such light sources.

In some embodiments, as illustrated in FIG. 5B, conductive traces on the rear side of the printed circuit board substrate 403 may include non-conductive regions 507 around some of the electrical sockets that correspond to the non-conductive regions on the front side of the printed circuit board substrate 403 described above. The example rear side of the printed circuit board may also include a plurality of resistors 509 that may couple the conductive traces 501 to the sockets surrounded by the non-conductive regions 507. Such resistors 509 may be used in embodiments of the invention as part of electrical connections among some of the light sources 401A, 401B. For example, in some embodiments that include both white light sources and long-wavelength light sources, one or the other type of light source may be less resistive. If those light sources were to be connected together in parallel (or in a grid of both series and parallel connections as illustrated in the example printed circuit board substrate 403), current would be applied predominantly to circuit branches with the less resistive type of light source, causing the more resistive type of light source to be less bright or not to function at all. The resistors 509 may be used to increase the resistivity associated with circuit branches having the less resistive type of light sources so that an approximately equal current is applied to circuit branches having both types of light sources. In some other implementations, rather than resistors 509, potentiometers may be used. In some such implementations, one or more additional copper layers may be used to isolate different types of light sources thereby allowing a reduction in the number of potentiometers used. Such potentiometers may allow resistivity to be controlled to accommodate a wide range of different light sources.

In embodiments with both white and long-wavelength light sources, the light sources may be arranged in any manner on the printed circuit board. In one example implementation, the light sources may be arranged in a checkerboard pattern so that the white and long-wavelength light sources are substantially evenly distributed about a surface of the printed circuit board substrate 403.

It should be understood that in some embodiments, different light source types may not be differently resistive, or only a single type of light source (e.g., long-wavelength) may be used. In such embodiments, the resistors 509 and non-conductive regions 507 may not be needed. Rather, the light sources 401A, 401B may be connected by the conductive traces 501 alone. FIGS. 6A and 6B illustrate a front and rear printed circuit board of an example embodiments in which only long-wavelength light sources having a similar resistivity are used. As is illustrated, the conductive traces do not include non-conductive gaps and resistors are not needed.

In some embodiments, the conductive traces 501 may be configured to be as large as possible on the printed circuit board substrate 403. Larger conductive traces may improve heat dissipation away from the light sources 401A, 401B thereby increasing the reliability and useful life of the light sources 401A, 401B. In one particular implementation, the printed circuit board substrate 403 may be approximately twenty-five millimeters tall by approximately nineteen millimeters wide. In such an implementation, the conductive traces 501 may be between approximately one and a half millimeters wide and approximately four millimeters wide.

In some embodiments, a bottom and top portion of the printed circuit board substrate 403 may not include any conductive traces 501. Such bottom and top portions may be used to position the printed circuit board within housing 407 without fear that a short circuit may result if the housing 407 includes a conductive element.

In some implementations, as shown in FIGS. 5A, 5B, 6A, and 6B, the printed circuit board substrate 403 may include attachment holes 511, which may be used to attach the printed circuit board substrate 403 to the housing 407. In some implementations, the attachment may be accomplished using one or more screws (not shown).

Figure 7A:
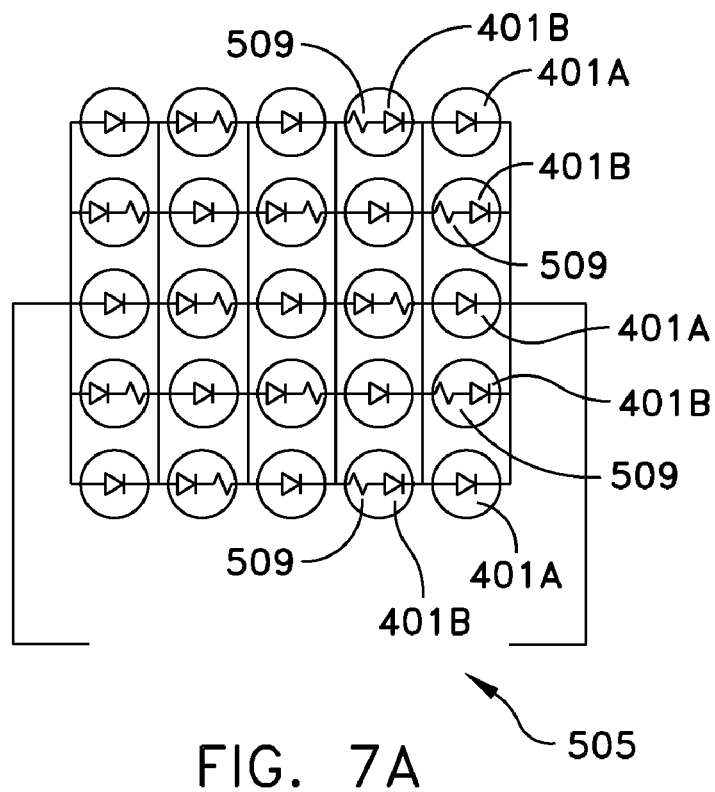
FIGS. 7A and 7B are electrical schematics of two printed circuit boards in accordance with embodiments of the invention.
Figure 7B:
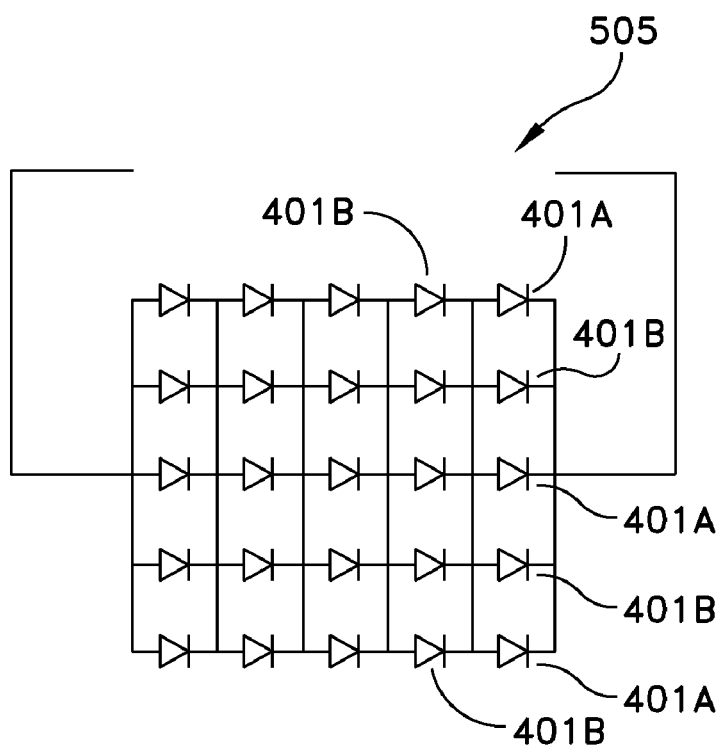

FIGS. 7A and 7B illustrate a simplified electrical schematic of the light sources 401A, 401B as they may be arranged in some embodiments. Power may be supplied to either embodiment from a power supply through the power inputs 505 (FIGS. 6A and 6B). FIG. 7A illustrates an example embodiment in which both long-wavelength light source and white light sources are used. In FIG. 7A, light sources indicated by 401B are long-wavelength light sources paired with resistors and light sources indicated by 401A are white light sources that are not paired with resistors. As is illustrated in FIG. 7A, the long-wavelength light sources (401B in FIG. 7A) may be paired with resistors 509 so that current is applied to each circuit branch at an approximately equal level, as is described above. In various implementations, the resistors may be disposed before or after the light sources to accommodate space and/or packing constraints. FIG. 7B illustrates an example embodiment in which all light sources 401A, 401B are a single type of light source (e.g., long-wavelength light sources). As illustrated, in such embodiments, additional resistors are not required. As is illustrated in both FIGS. 7A and 7B, the light sources may be connected together in a combination of both series and parallel to form a grid. In other embodiments, the light sources may be connected together in either series or parallel, or some other combination thereof.

In some embodiments, operation of the light sources 401A, 401B may include pulsing of the light sources. Current may be applied to the light sources 401A, 401B in pulses that are at least as long as is necessary to capture an image. In some implementations, such pulses may be less than approximately ten milliseconds long. In one particular implementation, such pulses may be approximately one millisecond long. After each pulse, some implementations may refrain from applying current to the light sources again for a period of time so that the light sources 401A, 401B may dissipate heat and achieve a thermal equilibrium. One implementation may include a maximum ten percent duty cycle in which the light sources 401A, 401B are pulsed for one millisecond and remain off for at least nine milliseconds before a next pulse. By limiting operation to such pulses, the heat generated by the light sources 401A, 401B may be minimized thereby extending the useful life and reliability of the light sources 401A, 401B.

In one example implementation, an operating current of the light sources 401A, 401B and resistance of the resistors 509 may be chosen so that each circuit branch experiences about eighty milliamps of current when in operation. In a five by five grid, as illustrated in FIGS. 5A, 5B, 6A, 6B, 7A, and 7B such a total operating current may be approximately four hundred milliamps. In the implementations shown in FIG. 7A in which NICHIA NSPW310BS white LEDs, as described above, and Marubeni L735-AU long-wavelength LEDs, as described above, are used as light sources, the resistors may include twenty-two Ohm resistors.

It should be understood that the example illumination device 209, imaging system 121, and printer 100 described and illustrated in the present disclosure are given as examples only and that the invention is not limited in design or construction to these examples. For example, although the example embodiments of the illumination device 400 is shown as including a five by five grid of LEDS, any arrangement (such as four by four grids) and/or type of long-wavelength and/or white light sources may be used with embodiments of the invention.

Figure 8:
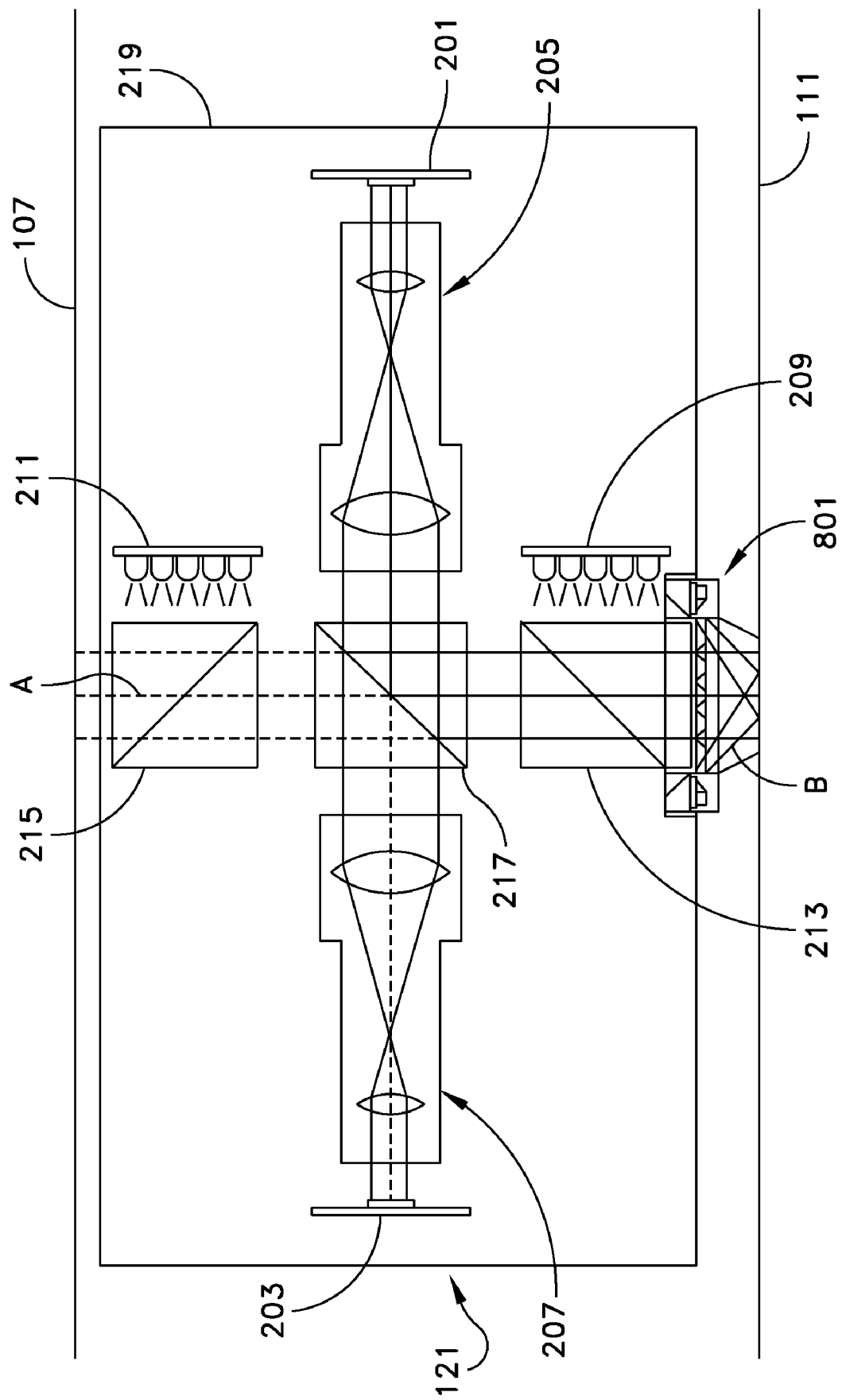
FIG. 8 is a diagram of an alternative imaging system in accordance with some embodiments of the invention.

FIG. 8 illustrates one alternative embodiment of the imaging system 121 discussed above. As illustrated, this alternative embodiment includes an off-axis illumination assembly 801 which may be mounted on or adjacent to the lowermost beam splitter 213. U.S. patent application Ser. No. 11/345,432 to Prince, entitled OFF-AXIS ILLUMINATING ASSEMBLY AND METHOD and filed Feb. 1, 2006, which is commonly assigned and hereby incorporated herein by reference, discusses off-axis illumination assemblies usable with some embodiments of the invention in more detail than the present disclosure.

The off-axis illumination assembly 801 may be configured to direct rays of light generally along or parallel to an axis B extending at an angle (e.g., between 30 and 60 degrees) with respect to the axis A. The off-axis-illumination assembly 801 may be designed to complement on-axis illumination provided, for example, by illumination device 209, thereby providing indirect light to more clearly see the rounded and faceted or otherwise irregular surfaces on the circuit board 111.

In some embodiments, the off-axis illumination assembly 801 may be configured to have an extremely low or narrow profile to fit within the space between the beam splitter 213 and the circuit board 111 or any other desired substrate. Because of this limited space, the off-axis illumination assembly 801 may be designed to direct light onto the circuit board 111 at an extremely close working distance while maintaining considerable control of local angles of incidence and the distribution and balance of light across target areas. The off-axis illumination assembly 801 may be designed to direct such light primarily by diffraction.

Figure 9:
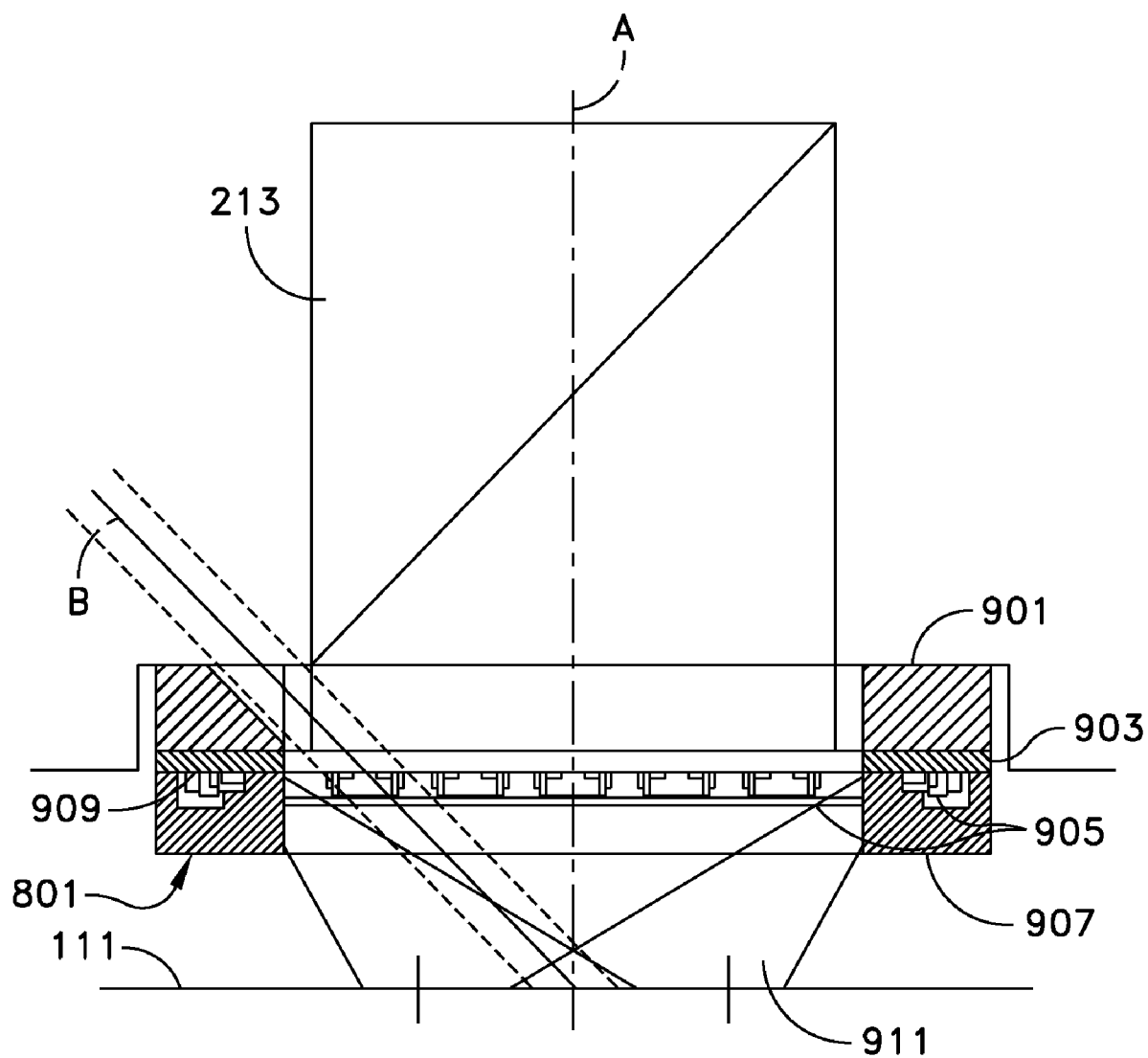
FIG. 9 is a diagram of an off-axis illumination assembly in accordance with some embodiments of the invention.

FIG. 9 illustrates a more detailed cross-sectional view of the off-axis illumination assembly 801. As is illustrated, the off-axis illumination assembly may include a rectangular-shaped mounting bracket 901, which may have four side rails (not shown) adapted to secure the operable components of the off-axis illumination assembly. In one embodiment, the mounting bracket 901 may be fabricated from a suitable lightweight material, such as aluminum. Other alternate lightweight materials may be provided, such as plastic or suitable metal alloys. The mounting bracket 901 may be attached to the frame 219 of the imaging system 121 directly below the beam splitter 213 by suitable fasteners, such as socket head screws (not shown). The mounting bracket 901 may not only support the components of the off-axis illumination assembly 801, but may further function as a heat sink to absorb heat generated by the off-axis illumination assembly. A printed circuit board substrate 903 may be secured to the downwardly facing surface of the mounting bracket 901 to provide power to the off-axis illumination assembly 801.

The mounting bracket 901 may further include slots to permit light, as used for 3-D triangulation, to pass at an angle generally along or parallel to axis B onto the target area of the circuit board 111 requiring imaging. The mounting bracket 901 may also provide strain relief for feed wires that may be connected to the off-axis illumination assembly via tight-tolerance wire passages that may have chamfered reliefs at the printed circuit board substrate interface to minimize the potential of a short circuit.

In certain embodiments, the off-axis illumination assembly 801 may comprise a light generating module embodying light emitting diodes, some of which are indicated at 905. The light emitting diodes 905 may be secured (e.g., soldered) to the bottom-facing surface of the printed circuit board substrate 903 and may be evenly spaced along the lengths of the rails of the mounting bracket 901. The printed circuit board substrate 903 may be in electrical communication with a power supply (not shown) to provide energy to the light emitting diodes 905. The light emitting diodes 905 may be disposed along a generally horizontal plane that is perpendicular to the vertical axis A of the optical path. The light emitting diodes 905 may be directed toward each other along the horizontal plane, and are not directed to the circuit board 111. The manner in which light generated by the light emitting diodes 905 is directed to the circuit board 111 will be discussed in greater detail below.

The off-axis illumination assembly 801 may further comprise a lens 907 secured to the mounting bracket 901 to cover the light emitting diodes 905. The lens 907 may be transparent or partially transparent, and in certain embodiments, fabricated from acrylic or glass. For example, the lens 907 may be fabricated from translucent acrylic to reduce object glare. Diffractive properties and the ability of the lens 907 to direct light are maintained when using translucent acrylic. When fabricated from acrylic material, the lens may be injection molded, where at least 1° of draft is required.

Figure 10A:
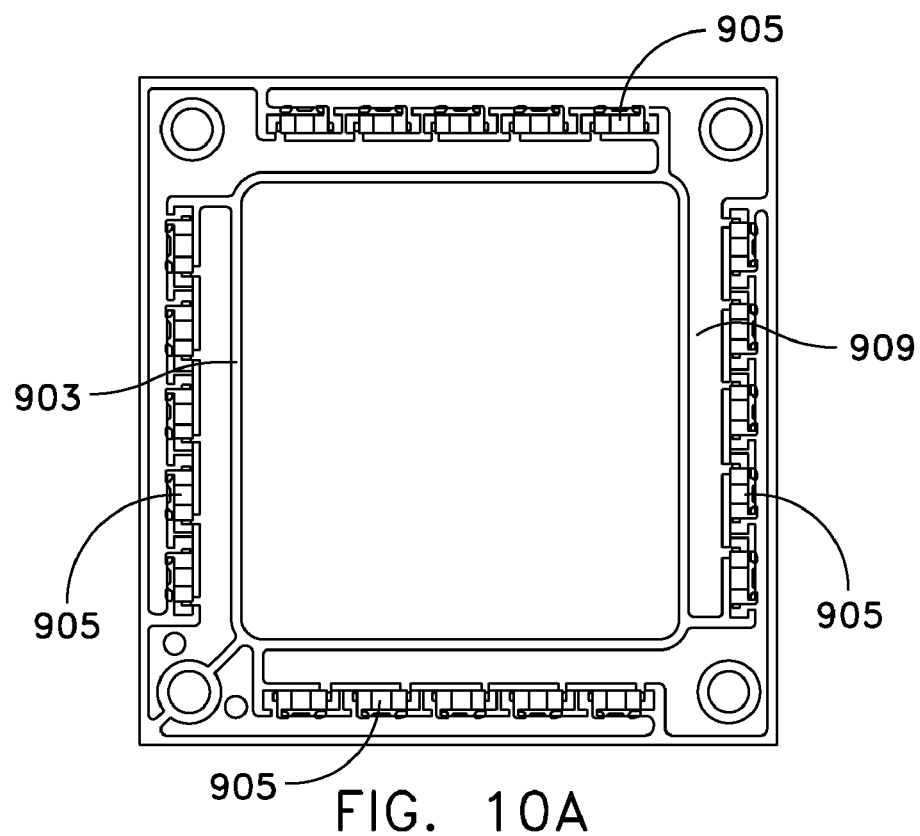
FIGS. 10A and 10B are diagrams of portions of the off-axis illumination assembly in accordance with some embodiments of the invention.
Figure 10B:
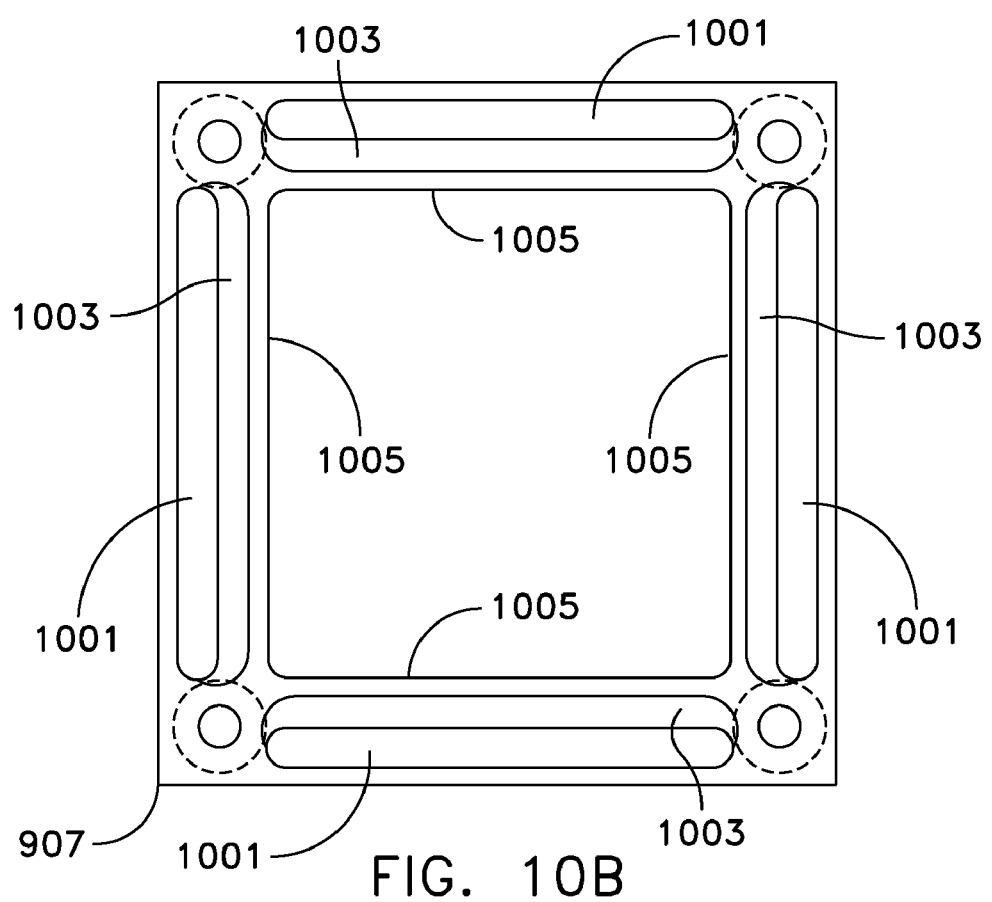

FIG. 10A illustrates an example bottom view of the LEDs arranged on the printed circuit board substrate 903. FIG. 10B illustrates an example view of the lens separated from the rest of off-axis illumination assembly 801. As illustrated, the lens 907 may include cavities 1001, which provide a space for the light emitting diodes 905 along the lengths of each side of the lens 907. The arrangement may be such that the mounting bracket 901, printed circuit board substrate 903, light emitting diodes 905 and lens 907 together define a low profile assembly that fits within the relatively small space provided between the beam splitter 213 and the circuit board 111. In certain embodiments, the total assembly has a thickness of approximately seven millimeters, and the nominal clearance between the off-axis illumination assembly 801 and the circuit board 111 is approximately five millimeters. In addition to directing light at a specified angle to a predefined area of the circuit board 111, the lens 907 is also designed to enclose and protect the light emitting diodes 905 and the printed circuit board substrate 903.

In some embodiments, each cavity 1001 of the lens 907 has a refractive surface 1003, which is adapted to direct light from the light emitting diodes 905 through refractive surfaces 1003 and 1005 and on toward the circuit board 111. Specifically, light directed to the refractive surfaces 1003 and 1005 may be refracted toward the predetermined area of the substrate (circuit board 111) generally along or parallel to axis B thereby providing off-axis illumination with respect to the viewing axis A. As shown, each cavity 1001 may be sized to receive the LEDs 905 comfortably within the cavity 1001. The refractive surface 1003 may slope toward a surface 1005 of the lens 907 that mates with the underside of the printed circuit board substrate 903. In one embodiment, the index of refraction of the refractive surface 1003 may be about 1.49. Light directed by the refractive surfaces 1003 and 1005 may be made to follow a parallel path to provide a constant illumination angle, or may be made to follow a fan-shaped path for a field position dependent angle. In some implementations, the lens 907 may have a thickness of approximately three millimeters.

The light generated by the off-axis illumination assembly 801 may follow a generally narrow fan-shaped geometry. The angle of the refractive surfaces 1003 and 1005 may be modified to change the angle of light propagation or manipulated to include multiple angles, facets and/or curvatures. For example, the light emitting diodes 905 and the refractive surfaces 1003 may be arranged in concentric or curved Fresnel-like sections, or may be arranged in linear, prism-like sections. Portions of light generated by each LED 905 that travel in a generally upward direction may be reflected off of a reflective surface 909 provided on the underside of the printed circuit board substrate 903 in front of the LEDs 905. The reflective surface 909 may be the bare material of the printed circuit board substrate 903, for example. In other embodiments, the reflective surface 909 may be fabricated from a mask material or from ink. In certain other embodiments, the reflective material may be bare copper or gold flashed copper, or a trace or pad having gold flashed copper. With gold flashed copper, oxidation is prevented for consistent reflective performance. In other embodiments, the reflective surface 909 may be a separately applied non-conductive film, vinyl, paper or a combination of these materials. The reflective surface 909 may be attached by using glue or a pressure sensitive material, for example. Alternatively, stray light generated by the light emitting diodes 905 may be absorbed by blackened surfaces, if required.

In the shown embodiment of the off-axis illumination assembly 801, the refractive surface 1003 of the lens 907 may be approximately at a 55° angle with respect to the vertical axis A. Each light emitting diode 905 may produce a geometry of light that is roughly the shape of an elliptical cone. Thus, light directed to the refractive surface 1003 and the reflective surface 909 may be adapted to be directed to the target or predetermined area of the printed circuit board 111. Any stray light generated by the light emitting diodes 905 may be redirected by reflection or absorbed by blackened surfaces, as required.

It should be understood that a person skilled in the art, given the benefit of this disclosure, may arrange the light emitting diodes 905 in any number of ways. For example, although a rectangular-shaped configuration is illustrated throughout the drawings, other shaped configurations are certainly contemplated. In one example, a circular mounting bracket containing the LEDs 905 positioned around a ring may be provided and fall within the scope of the invention. In another example, the mounting bracket 901 may be elliptical in shape. However, the rectangular shape (e.g., square) of the off-axis illumination assembly 801 offers the minimum physical size while still providing optimum off-axis angles of light to the predetermined area requiring imaging.

Referring back to FIG. 9, a fan of light 911 generated by a light emitting diode 905 is shown directed to the circuit board 111. The fan of light 911 may be generated by each light emitting diode 905 provided around the mounting bracket 901 to splash off-axis light on the circuit board 111. Light directed from the refractive surfaces 1003 and 1005, and from the reflective surface 909 provide the fan of light 911 that extends generally along or substantially parallel to the axis B, which is disposed at an angle with respect to the viewing axis A and light generated, for example, by the illumination device 209. The fan of light 911 generated by the off-axis illumination assembly 801 better illuminates irregular surfaces of solder paste or other substances deposited on the circuit board 111.

In one embodiment, the light emitting diodes 905 are of the type sold by Nichia Corporation of Detroit, Mich. under Model No. NASW008B, with brightness of ranks U2 and V1 each having an average brightness of approximately two thousand millicandelas during continuous operation.

Figure 11:
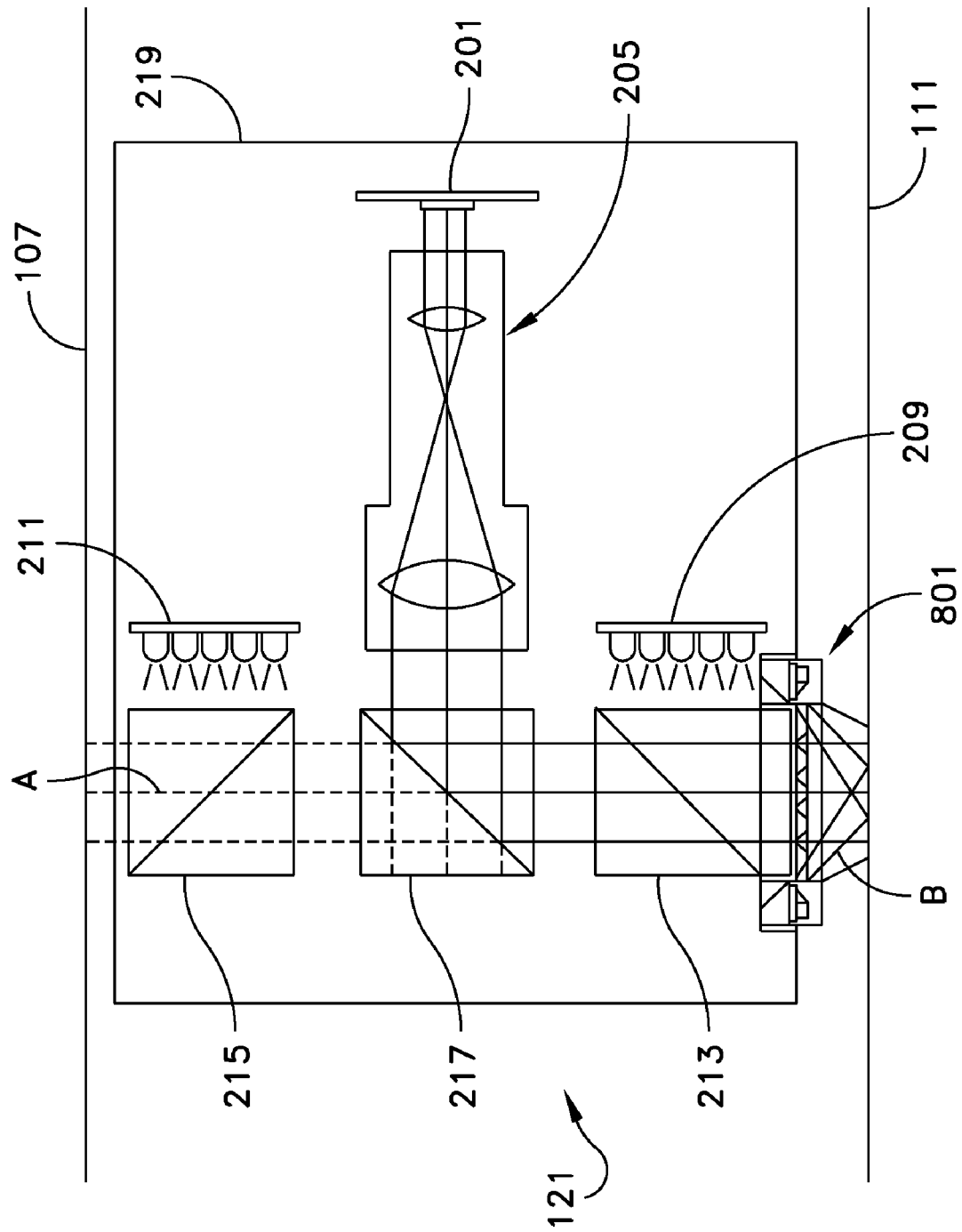
FIG. 11 is a diagram of another alternative imaging system in accordance with some embodiments of the invention.

As shown, the off-axis illumination assembly 801 is provided on the imaging system 121 employing two cameras 201, 203. However, as illustrated in FIG. 11, the off-axis illumination assembly 801 may be provided on an imaging system 123 employing only one camera 201 and still fall within the scope of the invention. Whether employing a single or dual camera arrangement, the controller 103 is adapted to control the movement and/or operation of the imaging system 121 to capture an image of the circuit board 111. It should also be understood that a second off-axis illumination assembly or an alternative off-axis illumination assembly may be configured to illuminate the stencil 107 if desired. Specifically, an off-axis illumination assembly, identical to assembly 801, may be configured or assembled on beam splitter 215, in the same manner that assembly 801 is mounted on beam splitter 213.

Figure 12:
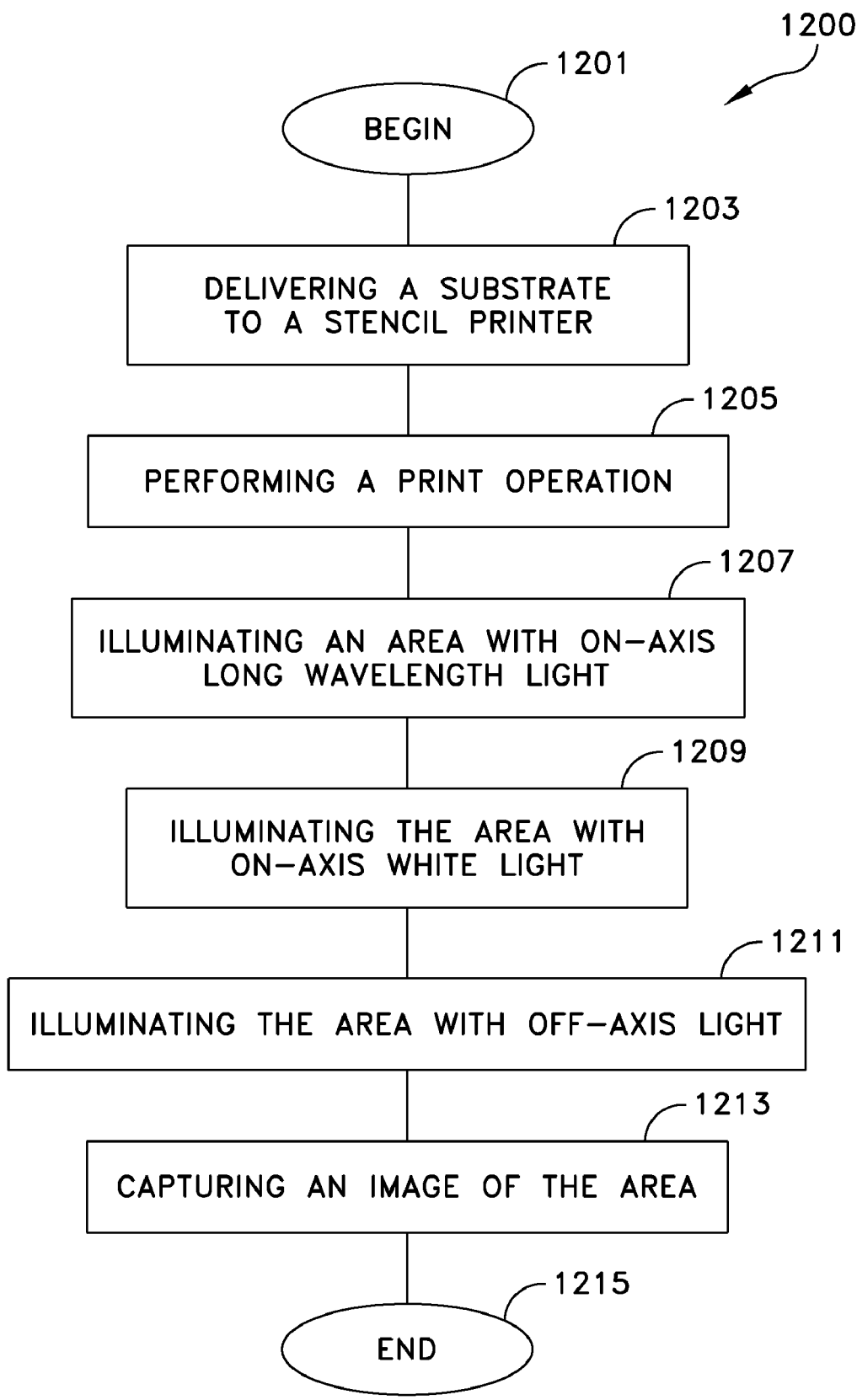
FIG. 12 is a method for dispensing solder paste onto a substrate in accordance with some embodiments of the invention.

Turning to FIG. 12, a method for dispensing solder onto electronic pads of a circuit board is generally designated at 1200. The method begins at block 1201. As indicated at block 1203, the method 1200 may include delivering a substrate (e.g., the circuit board 111) to the stencil printer (e.g., via a conveyor system). With reference to FIG. 1, the circuit board 111 is delivered to the printer via the conveyor rails 113, 115. Once delivered, the circuit board 111 may be positioned within a print nest on top of the support assembly 117, precisely aligned with the stencil 107 using the imaging system 121, and raised by the support assembly 117 so that it is maintained in a print position. In some implementations, a bar code or other identification element may be read from the substrate using the imaging system 121 for tracking/identification purposes.

As indicated at block 1205, the method 1200 may include performing a print operation. Referring to FIG. 1, performing the print operation may include lowering the dispensing head 109 to engage the stencil 107 to deposit solder paste on the circuit board 111. Once printing is completed, inspection of the circuit board 111 and/or stencil 107 may take place. Stencil inspection may also be performed independently and concurrently as circuit boards are transported to and from the print nest area.

Specifically, as indicated at block 1207, a predefined area of the circuit board 111 (and/or stencil 107) may be imaged by illuminating the predefined area with on-axis long-wavelength light. The on-axis long-wavelength light may be generated, for example, by an on-axis long-wavelength light source, as described above. At the same time or at a different time, as indicated at block 1209, in some embodiments, the predefined area may be illuminated with on-axis white light. The on-axis light may be generated, for example, by an on-axis white light source, as described above. At the same time or at a different time, as indicated at block 1211, the predefined area may also be illuminated with off-axis light. The off-axis light may be generated by an off-axis light source, as described above.

As indicated at block 1213, once the circuit board 111 (and/or stencil 107) is adequately illuminated, the camera (e.g., 201, 203) may capture an image of the predefined area. The process 1200 may then end at block 1215. It should be understood that not all embodiments of the process 1200 or similar processes may include illumination with white light and/or off-axis light.

In some embodiments, a subsequent predefined area of the circuit board 111 or the stencil 107 may be imaged. The imaging of multiple predefined areas of the circuit board 111 may be executed by moving the imaging system 121 from the first predefined area to the second predefined area. Under the direction of the controller 103, the imaging system 121 may sequentially moves to other predefined areas to capture images for inspection purposes, for example. In other embodiments, the method may include capturing an image of an area of the stencil 107 instead of or in addition to capturing an image of the circuit board 111.

In one embodiment, the imaging system 121 and/or controller 103 may be used to perform a threshold based contrast recognition method. In such a method, a brightness level at a location within a captured image may be compared to a threshold value. If the brightness level is above the threshold level, the imaging system 121 and/or controller 103 may determine that the location does not include a solder paste deposit. If the brightness level is below the threshold level, the imaging system 121 and/or controller 103 may determine that the location does include a solder paste deposit. Such methods are well-known in the art.

In one embodiment, the imaging system 121 and/or controller 103 may be used to perform a texture recognition method, such as the method disclosed in U.S. Pat. No. 6,738,505 to Prince, entitled METHOD AND APPARATUS FOR DETECTING SOLDER PASTE DEPOSITS ON SUBSTRATES, which is owned by the assignee of the invention and hereby incorporated herein by reference. U.S. Pat. No. 6,891,967 to Prince, entitled SYSTEMS AND METHODS FOR DETECTING DEFECTS IN PRINTED SOLDER PASTE, which is also owned by the assignee of the invention and hereby incorporated herein by reference, furthers the teachings of U.S. Pat. No. 6,738,505. Specifically, these patents teach texture recognition methods for determining whether solder paste is properly deposited onto predetermined regions, e.g., copper contact pads, located on a printed circuit board.

Figure 13:
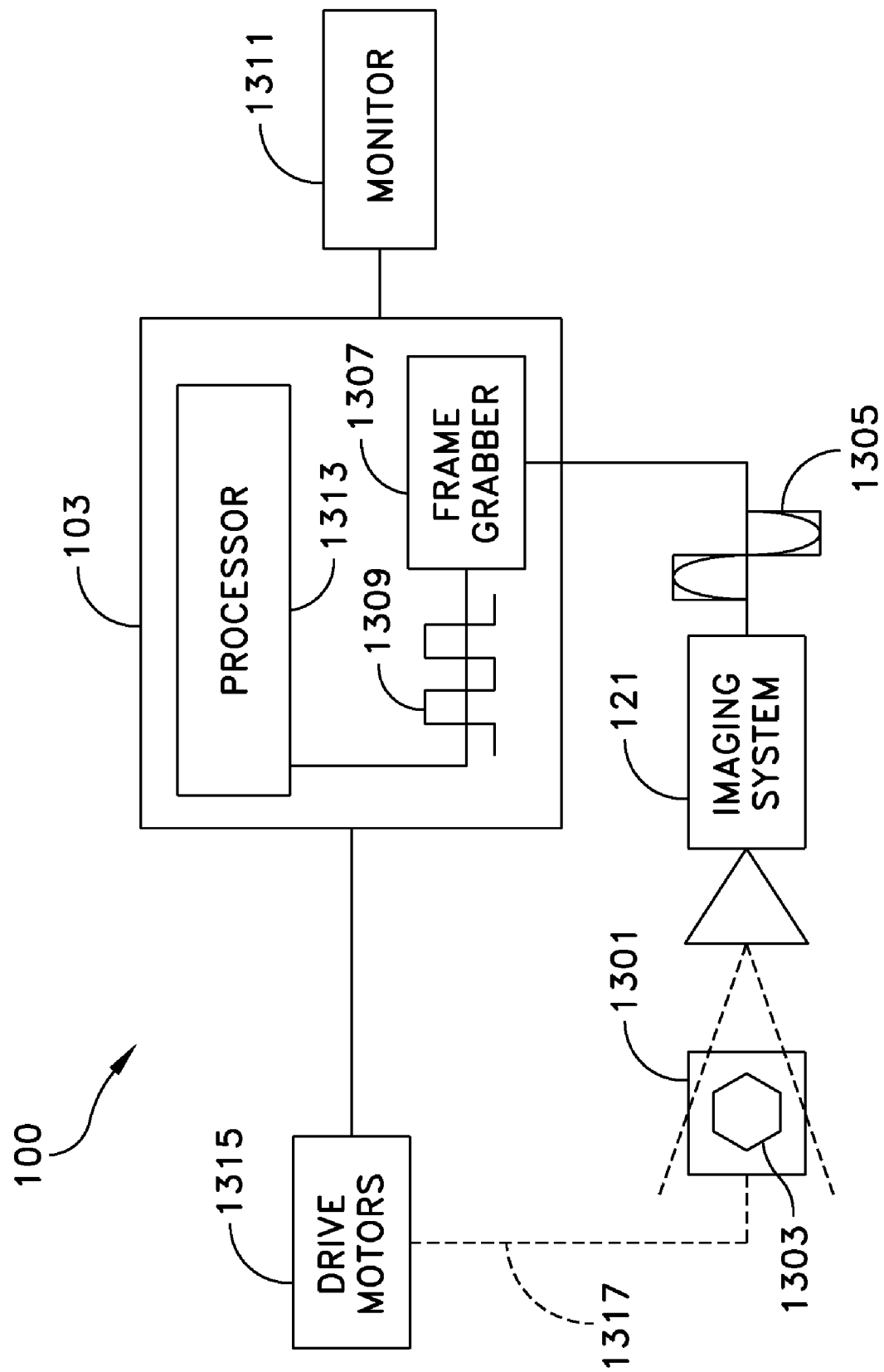
FIG. 13 is a diagram of a stencil printer in operation in accordance with some embodiments of the invention.
Figure 14A:
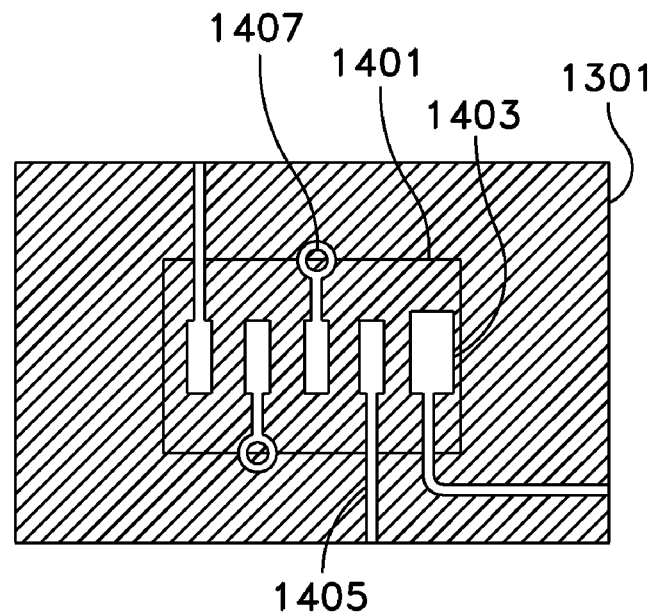
FIGS. 14A and 14B are views of a circuit board in accordance with some embodiments of the invention.
Figure 14B:
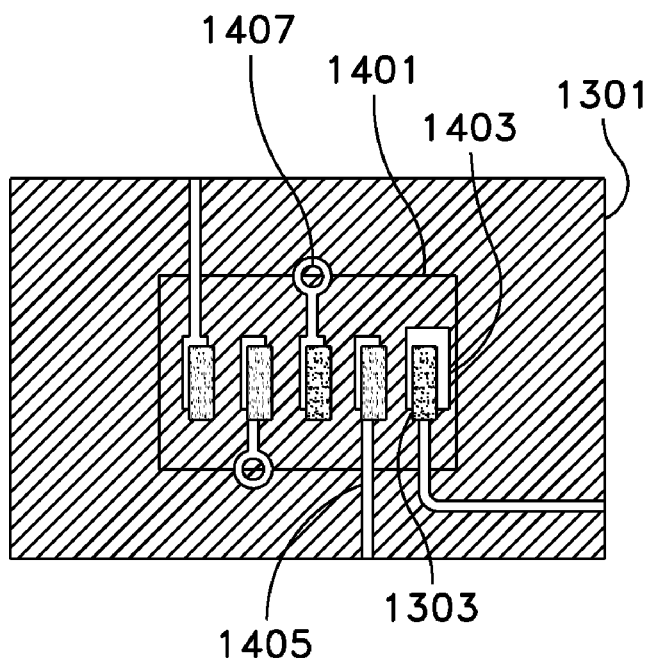

With reference to FIG. 13, in one embodiment, the stencil printer 100 is shown inspecting a substrate 1301 having a substance 1303 deposited thereon. The substrate 1301 may embody a printed circuit board (e.g., the circuit board 111), wafer, or similar flat surface, and the substance 1303 may embody solder paste, or other viscous materials, such as glues, encapsulents, underfills, and other assembly materials suitable for attaching electronic components onto printed circuit boards or wafers. As shown in FIGS. 14A and 14B, the substrate 1301 may have a region of interest 1401 and contact regions 1403. The substrate 1301 may further includes traces 1405 and vias 1407, which are used to interconnect components mounted on the substrate 1301, for example. FIG. 14A illustrates the substrate 1301 without substances deposited on any of the contact regions 1403. FIG. 14B illustrates the substrate 1301 having substances 1303, e.g., solder paste deposits, distributed on the contact regions 1403. On the substrate 1301, the contact regions 1403 are distributed across the region of interest 1401.

FIG. 14B particularly shows a misalignment of a deposit of the substance 1303 with the contact regions 1403. As shown, each of the substance 1303 deposits (e.g., solder paste deposits) is partially touching one of the contact regions 1403. To ensure good electrical contact and to prevent bridging between adjacent contact regions, e.g., copper contact pads, the substance 1303 deposits should be aligned to respective contact regions 1403 within specific tolerances. Contrast and/or texture recognition methods such as those described above may detect misaligned substance 1303 deposits on contact regions 1403, and as a result, generally improve the manufacturing yield of the substrates 1301. In situation in which the contact regions 1403 are provided having a non-reflective or less-reflective coating, such contrast recognition methods may be more effective when long-wavelength illumination is used.

Referring back to FIG. 13, in one embodiment, a method for solder paste inspection includes using the imaging system 121 to capture an image of the substrate 1301 having the substance 1303 deposited thereon. The imaging system 121 may be configured to transmit a real-time signal 1305 to an appropriate digital communication port or dedicated frame grabber 1307. The digital port may include types commonly known as USB, Ethernet, or Firewire (IEEE 1394). The real-time signal 1305 corresponds to an image of the substrate 1301 having the substance 1303 deposited thereon. Once received, the port or frame grabber 1307 may create image data 1309 which may be displayed on a monitor 1311. In one embodiment, the image data 1309 is divided into a predetermined number of pixels, each having a brightness value from 0 to 255 gray levels. Such brightness values may be compared to one or more threshold values to determine whether a solder paste deposit is present. In one embodiment, the signal 1305 represents a real-time image signal of the substrate 1301 and the substance 1303 deposited thereon. In some embodiments, the image may be stored in local memory (e.g., RAM) and transmitted to the controller 103 on demand, as required.

The port or frame grabber 1307 may be electrically connected to the controller 103, which includes a processor 1313. The processor 1313 may calculate statistical variations in texture and/or contrast in the image data 1309 of the substance 1303. Such statistical variations in texture contrast in the image data 1309 of the substance 1303 may be calculated independent of relative brightness of non-substance background features on the substrate 1301, thereby enabling the processor 1313 to determine the location of the substance 1303 on the substrate 1301 and compare the location of the substance 1303 with a desired location. In one embodiment, if the comparison between the desired location and the actual location of the substance 1303 reveals misalignment exceeding a predefined threshold, the processor 1313 may respond with adaptive measures to reduce or eliminate the error, may reject the substrate, may terminate a process, and/or may trigger an alarm via the controller.

The controller 103 may be electrically connected to drive motors 1315 of the stencil printer 100 to facilitate the alignment of the stencil 107 and the substrate 1301 as well as other motion related to the printing process. The controller 103 may be part of a control loop 1317 that includes the drive motors 1315 of the stencil printer 100, the imaging system 121, the frame grabber 1307 and the processor 1313. As part of an adaptive measure in response to a misaligned depositing of the substance 1303, the controller 103 may send a signal to adjust the alignment of the stencil 107.

In yet another example embodiment, the stencil 107 and/or the circuit board 111 may move relative to the imaging system 121 to take images of the stencil and the board, respectively. For example, the stencil 107 may be translated away from the print nest and moved over or under the imaging system 121, which may be stationary. Similarly, the circuit board 111 may be shuttled away from the print nest and moved over or under the imaging system 121. The camera (e.g., camera 201) of the imaging system 121 may then take an image of the stencil 107 and/or circuit board 111.

In still another embodiment, the imaging system 121 may be employed within a dispenser designed to dispense viscous or semi-viscous materials, such as solder paste, glues, encapsulents, underfills, and other assembly materials on a substrate, such as a printed circuit board. Such dispensers may be of the type sold by Speedline Technologies, Inc., under the brand name CAMALOT®.

In various embodiments, it should be recognized that by using long-wavelength illumination, thresholding based contrast recognition techniques may be used to improve the inspection of solder paste deposits on a circuit board. Long-wavelength illumination may be particularly useful to inspect solder paste deposits on a circuit board in which pads are coated in non-reflective or less-reflective coatings. By using long-wavelength illumination is such circumstances, the long-wavelength light may penetrate the otherwise non-reflective or less-reflective coating and be reflected to a camera as if the coating were not present, thereby allowing threshold-based imaging techniques to function properly.

From the above description, it should be observed that the imaging system 121 of the invention is particularly suited for capturing uniformly illuminated images under a variety of conditions as required to perform contrast and/or texture recognition methods while providing efficient real-time, closed-loop control. Also, since the long-wavelength light allows for penetration of non-reflective and less-reflective coatings that may be used on some substrates, such an illumination system 121 may be particularly useful to analyze depositing of substances on substrates having such coatings.

It should be recognized that adding white illumination to the long-wavelength illumination may improve the sharpness of images captured compared to those captured using long-wavelength illumination alone. Such improved sharpness may allow an imaging system to perform operations that require fine details, such as alignment of circuit board and stencil, texture-based paste detection, and/or reading bar codes.

It should also be recognized that adding off-axis illumination to long-wavelength illumination to improve the robustness of two-dimensional texture-based solder paste inspection, especially in circumstances where there is less than ideal solder paste deposit geometry. The off-axis illumination assembly may be particularly designed to improve the ability to view such defects. Poorly defined solder paste deposits usually indicate the presence of significant defects and trends that, if left unchecked, might eventually lead to catastrophic circuit board defects.

While the invention has been shown and described with references to particular embodiments thereof, those skilled in the art will understand that various changes in form and details may be made therein without departing from the scope of the invention, which is limited only to the following claims.

What is claimed is:

1. A stencil printer apparatus for depositing a solder paste onto the surface of the electronic substrate, the stencil printer comprising:
   a frame;
   a stencil coupled to the frame, the stencil having a plurality of apertures;
   a dispenser coupled to the frame, the stencil and the dispenser being configured to deposit the solder paste onto the electronic substrate;

an imaging system constructed and arranged to capture an image of the electronic substrate, the imaging system comprising:
- a camera element configured to capture the image of at least the portion of the surface of the electronic substrate, and
- a first illumination element comprising a long-wavelength light source configured to illuminate at least the portion of the surface of the electronic substrate by generating long-wavelength light, wherein the first illumination element includes an on-axis illumination element configured to generate the long-wavelength light substantially along a first axis that is generally perpendicular to the surface of the electronic substrate, and
- an off-axis illumination element configured to generate light substantially along a second axis that extends at an angle with respect to the first axis; and
- a controller coupled to the imaging system and configured to control movement of the imaging system to capture the image.

2. The apparatus of claim 1, wherein the long-wavelength light includes infrared light.

3. The apparatus of claim 2, wherein the infrared light includes near-infrared light.

4. The apparatus of claim 1, wherein the long-wavelength light includes light having a wavelength greater than about 670 nanometers.

5. The apparatus of claim 4, wherein the long-wavelength light includes light having a wavelength less than about 825 nanometers.

6. The apparatus of claim 5, wherein the long-wavelength light includes light having a wavelength of about 735 nanometers.

7. The apparatus of claim 1, wherein the long-wavelength light source comprises at least one long-wavelength LED configured to generate the long-wavelength light.

8. The apparatus of claim 7, wherein the at least one long-wavelength LED includes a plurality of long-wavelength LEDs.

9. The apparatus of claim 1, wherein the on-axis illumination element further comprises a white light source configured to illuminate at least the portion of the surface of the electronic substrate by generating white light substantially along the first axis.

10. The apparatus of claim 1, wherein the image includes a representation of solder paste on a pad of the electronic substrate.

11. A stencil printer apparatus for depositing a solder paste onto the surface of the electronic substrate, the stencil printer comprising:
- a frame;
- a stencil coupled to the frame, the stencil having a plurality of apertures;
- a dispenser coupled to the frame, the stencil and the dispenser being configured to deposit the solder paste onto the electronic substrate;
- an imaging system constructed and arranged to capture an image of the electronic substrate, the imaging system comprising:
  - a camera element configured to capture the image of at least the portion of the surface of the electronic substrate, and
  - a first illumination element comprising a long-wavelength light source configured to illuminate at least the portion of the surface of the electronic substrate by generating long-wavelength light; and
- a controller coupled to the imaging system and configured to control movement of the imaging system to capture the image, wherein the first illumination element further comprises a white light source configured to illuminate at least the portion of the surface of the electronic substrate by generating white light.

12. The apparatus of claim 11, wherein the long-wavelength light source comprises at least one long-wavelength LED configured to generate the long-wavelength light and the white light source comprises at least one white LED configured to generate the white light.

13. The apparatus of claim 12, wherein the first illumination element is configured such that when generating the long-wavelength light and the white light, at least one first circuit branch to which the at least one long-wavelength LED is coupled and at least one second circuit branch to which the at least one white LED is coupled both experience a substantially similar current.

14. The apparatus of claim 13, wherein the substantially similar current is about eighty milliamps.

15. The apparatus of claim 13, wherein the first illumination element includes at least one resistor coupled to at least one of the at least one first circuit branch and the at least one second circuit branch such that when generating the long-wavelength light and the white light, the at least one first circuit branch and the at least one second circuit branch experience the substantially similar current.

16. The apparatus of claim 11, wherein the first illumination element is configured to illuminate at least the portion of the surface of the electronic substrate by substantially simultaneously generating the white light and the long-wavelength light.

17. A stencil printer apparatus for depositing a solder paste onto the surface of the electronic substrate, the stencil printer comprising:
- a frame;
- a stencil coupled to the frame, the stencil having a plurality of apertures;
- a dispenser coupled to the frame, the stencil and the dispenser being configured to deposit the solder paste onto the electronic substrate;
- an imaging system constructed and arranged to capture an image of the electronic substrate, the imaging system comprising:
  - a camera element configured to capture the image of at least the portion of the surface of the electronic substrate, and
  - a first illumination element comprising a long-wavelength light source configured to illuminate at least the portion of the surface of the electronic substrate by generating long-wavelength light, wherein the first illumination element further comprises at least one diffuser configured such that the long-wavelength light substantially uniformly illuminates at least the portion of the electronic substrate; and
- a controller coupled to the imaging system and configured to control movement of the imaging system to capture the image.

18. A stencil printer apparatus for depositing a solder paste onto the surface of the electronic substrate, the stencil printer comprising:
- a frame;
- a stencil coupled to the frame, the stencil having a plurality of apertures;

a dispenser coupled to the frame, the stencil and the dispenser being configured to deposit the solder paste onto the electronic substrate;

an imaging system constructed and arranged to capture an image of the electronic substrate, the imaging system comprising:

a camera element configured to capture the image of at least the portion of the surface of the electronic substrate, and a first illumination element comprising a long-wavelength light source configured to illuminate at least the portion of the surface of the electronic substrate by generating long-wavelength light; and a controller coupled to the imaging system and configured to control movement of the imaging system to capture the image, wherein the controller includes a processor configured to perform a first contrast recognition process on the image to determine the accuracy of a desired solder paste deposit on at least one pad of the electronic substrate.

19. The apparatus of claim 18, wherein the imaging system is further configured to capture an image of the stencil, and the processor is further configured to perform a second contrast recognition process on the image of the stencil to detect an undesired solder paste deposit on the stencil.

20. An imaging apparatus for capturing an image of at least a portion of a surface of an electronic substrate, the imaging apparatus comprising:

a camera element configured to capture the image of at least the portion of the surface of the electronic substrate;

a first illumination element comprising a long-wavelength light source configured to illuminate at least the portion of the surface of the electronic substrate by generating long-wavelength light, wherein the first illumination element includes an on-axis illumination element configured to generate the long-wavelength light substantially along a first axis that is generally perpendicular to the surface of the electronic substrate and an off-axis illumination element configured to generate light substantially along a second axis that extends at an angle with respect to the first axis.

21. The apparatus of claim 20, wherein the long-wavelength light includes infrared light.

22. The apparatus of claim 21, wherein the infrared light includes near-infrared light.

23. The apparatus of claim 20, wherein the long-wavelength light includes light having a wavelength greater than about 670 nanometers.

24. The apparatus of claim 23, wherein the long-wavelength light includes light having a wavelength less than about 825 nanometers.

25. The apparatus of claim 24, wherein the long-wavelength light includes light having a wavelength of about 735 nanometers.

26. The apparatus of claim 20, wherein the long-wavelength light source comprises at least one long-wavelength LED configured to generate the long-wavelength light.

27. The apparatus of claim 26, wherein the at least one long-wavelength LED includes a plurality of long-wavelength LEDs.

28. The apparatus of claim 20, wherein the first illumination element further comprises a white light source configured to illuminate at least the portion of the surface of the electronic substrate by generating white light.

29. The apparatus of claim 28, wherein the long-wavelength light source comprises at least one long-wavelength LED configured to generate the long-wavelength light and the white light source comprises at least one white LED configured to generate the white light.

30. The apparatus of claim 29, wherein the first illumination element is configured such that when generating the long-wavelength light and the white light, at least one first circuit branch to which the at least one long-wavelength LED is coupled and at least one second circuit branch to which the at least one white LED is coupled both experience a substantially similar current.

31. The apparatus of claim 30, wherein the substantially similar current is about eighty milliamps.

32. The apparatus of claim 30, wherein the first illumination element includes at least one resistor coupled to at least one of the at least one first circuit branch and the at least one second circuit branch such that when generating the long-wavelength light and the white light, the at least one first circuit branch and the at least one second circuit branch experience the substantially similar current.

33. The apparatus of claim 28, wherein the first illumination element is configured to illuminate at least the portion of the surface of the electronic substrate by substantially simultaneously generating the white light and the long-wavelength light.

34. The apparatus of claim 20, wherein the on-axis illumination element further comprises a white light source configured to illuminate at least the portion of the surface of the electronic substrate by generating white light substantially along the first axis.

35. The apparatus of claim 20, wherein the image includes a representation of solder paste on a pad of the electronic substrate.

36. The apparatus of claim 20, wherein the imaging system is further configured to capture an image of a stencil that includes a representation of undesired solder paste on the stencil.

37. An imaging apparatus for capturing an image of at least a portion of a surface of an electronic substrate, the imaging apparatus comprising:

a camera element configured to capture the image of at least the portion of the surface of the electronic substrate; and a first illumination element comprising a long-wavelength light source configured to illuminate at least the portion of the surface of the electronic substrate by generating long-wavelength light, wherein the first illumination element further comprises at least one diffuser configured such that the long-wavelength light substantially uniformly illuminates at least the portion of the electronic substrate.

38. An imaging apparatus for capturing an image of at least a portion of a surface of an electronic substrate, the imaging apparatus comprising:

a camera element configured to capture the image of at least the portion of the surface of the electronic substrate; and a first illumination element comprising means for illuminating at least the portion of the surface of the electronic substrate with long-wavelength light, wherein the means for illuminating the at least the portion of the surface includes an on-axis means for illuminating the at least the portion of the surface by generating the long-wavelength light substantially along a first axis that is generally perpendicular to the surface of the electronic substrate, and an off-axis illumination element configured to generate light substantially along a second axis that extends at an angle with respect to the first axis.

39. The apparatus of claim 38, wherein the long-wavelength light includes infrared light.

40. The apparatus of claim 39, wherein the infrared light includes near-infrared light.

41. The apparatus of claim 38, wherein the long-wavelength light includes light having a wavelength greater than about 670 nanometers.

42. The apparatus of claim 41, wherein the long-wavelength light includes light having a wavelength less than about 825 nanometers.

43. The apparatus of claim 42, wherein the long-wavelength light includes light having a wavelength of about 735 nanometers.

44. The apparatus of claim 38, wherein the first illumination element further comprises a white light source configured to illuminate at least the portion of the surface of the electronic substrate with white light.

45. The apparatus of claim 38, wherein the on-axis means further comprises a white light source configured to illuminate at least the portion of the surface of the electronic substrate with white light.

46. The apparatus of claim 38, wherein the means for illuminating at least the portion of the surface of the electronic substrate comprises at least one long-wavelength LED.

47. An imaging apparatus for capturing an image of at least a portion of a surface of an electronic substrate, the imaging apparatus comprising:
a camera element configured to capture the image of at least the portion of the surface of the electronic substrate; and
a first illumination element comprising means for illuminating at least the portion of the surface of the electronic substrate with long-wavelength light, wherein the means for illuminating at least the portion of the surface of the electronic substrate further comprises a diffuser configured so that the long-wavelength light substantially uniformly illuminates the portion of the electronic substrate.

48. A method of dispensing a solder paste onto a surface of an electronic substrate, the method comprising:
delivering the electronic substrate to a stencil printer;
depositing the solder paste onto the surface of the electronic substrate;
illuminating at least a portion of the surface of the electronic substrate with long-wavelength light that is generated by a long-wavelength light source;
directing the long wavelength light substantially along a first axis that is generally perpendicular to the surface of the electronic substrate;
illuminating at least the portion of the surface of the electronic substrate with light directed substantially along a second axis that extends at an angle with respect to the first axis; and
capturing an image of at least the portion of the surface of the electronic substrate.

49. The method of claim 48, wherein the long-wavelength light includes infrared light.

50. The method of claim 49, wherein the infrared light includes near-infrared light.

51. The method of claim 48, wherein the long-wavelength light includes light having a wavelength greater than about 670 nanometers.

52. The method of claim 51, wherein the long-wavelength light includes light having a wavelength less than about 825 nanometers.

53. The method of claim 52, wherein the long-wavelength light includes light having a wavelength of about 735 nanometers.

54. The method of claim 48, further comprising determining an accuracy of a solder paste deposit on the surface of the electronic substrate.

55. The method of claim 54, wherein determining the accuracy of the solder paste deposit includes comparing at least a portion of the image to at least one threshold value.

56. The method of claim 48, further comprising illuminating at least the portion of the surface of the electronic substrate with white light directed substantially along the first axis.

57. A method of dispensing a solder paste onto a surface of an electronic substrate, the method comprising:
delivering the electronic substrate to a stencil printer;
depositing the solder paste onto the surface of the electronic substrate;
illuminating at least a portion of the surface of the electronic substrate with long-wavelength light that is generated by a long-wavelength light source;
illuminating at least the portion of the surface of the electronic substrate with white light; and
capturing an image of at least the portion of the surface of the electronic substrate.

* * * * *

UNITED STATES PATENT AND TRADEMARK OFFICE
CERTIFICATE OF CORRECTION

| | | |
|---|---|---|
| PATENT NO. | : 7,710,611 B2 | Page 1 of 1 |
| APPLICATION NO. | : 11/707757 | |
| DATED | : May 4, 2010 | |
| INVENTOR(S) | : David P. Prince | |

It is certified that error appears in the above-identified patent and that said Letters Patent is hereby corrected as shown below:

Column 13, line 53, delete "SB" and insert --5B--.

Signed and Sealed this

Nineteenth Day of October, 2010

David J. Kappos
*Director of the United States Patent and Trademark Office*